(12) United States Patent
Loderer et al.

(10) Patent No.: US 10,583,239 B2
(45) Date of Patent: Mar. 10, 2020

(54) FLUID FLOW RATE MEASURING AND GAS BUBBLE DETECTING APPARATUS

(71) Applicants: Maquet Cardiopulmonary AG, Rastatt (DE); Christian Loderer, Rastatt (DE); Wesley Scott Ashton, Bloomingdale, NJ (US)

(72) Inventors: Christian Loderer, Rastatt (DE); Wesley Scott Ashton, Bloomingdale, NJ (US)

(73) Assignee: MAQUET CARDIOPULMONARY GmbH, Rastatt (DE)

( * ) Notice: Subject to any disclaimer, the term of this patent is extended or adjusted under 35 U.S.C. 154(b) by 130 days.

(21) Appl. No.: 15/553,917

(22) PCT Filed: Feb. 26, 2016

(86) PCT No.: PCT/US2016/019771
§ 371 (c)(1),
(2) Date: Aug. 25, 2017

(87) PCT Pub. No.: WO2016/138380
PCT Pub. Date: Sep. 1, 2016

(65) Prior Publication Data
US 2018/0110913 A1    Apr. 26, 2018

Related U.S. Application Data

(60) Provisional application No. 62/121,674, filed on Feb. 27, 2015.

(51) Int. Cl.
*A61M 1/36* (2006.01)
*A61B 8/08* (2006.01)
(Continued)

(52) U.S. Cl.
CPC .............. *A61M 1/3626* (2013.01); *A61B 5/01* (2013.01); *A61B 5/026* (2013.01);
(Continued)

(58) Field of Classification Search
CPC ......... A61M 1/3626; A61B 5/026; A61B 8/06
See application file for complete search history.

(56) References Cited

U.S. PATENT DOCUMENTS 3,053,083 A    9/1962   Stough et al.
5,167,144 A    12/1992  Schneider
(Continued)

FOREIGN PATENT DOCUMENTS

CN    101184517 A    5/2008
CN    103308105 A    9/2013
(Continued)

OTHER PUBLICATIONS

International Search Report and Written Opinion of corresponding International Application No. PCT/US2016/019771 dated May 2, 2016.
(Continued)

*Primary Examiner* — Justin N Olamit
(74) *Attorney, Agent, or Firm* — Wesley Scott Ashton

(57) ABSTRACT

A fluid flow sensing and bubble detecting apparatus includes a housing comprising a channel configured to receive a tube through which fluid flows; a sensor apparatus disposed within the housing, which includes a first sensor operable to measure flow rate of fluid and to detect bubbles in flowing fluid; and a temperature sensor operable to detect temperature of the flowing fluid; and a processor connected to receive fluid flow rate data obtained by the first sensor, to receive bubble detection data obtained by the first sensor, and to receive fluid temperature data obtained by the temperature sensor, wherein when a tube through which fluid
(Continued)

flows is disposed in the channel of the housing, the first sensor measures the flow rate of the flowing fluid and detects bubbles therein, and the temperature sensor measures the temperature of the flowing fluid, and the processor calculates in a short period of time a fluid flow rate corrected for temperature. All sensors are non-invasive and have no direct contact to the fluid in the tube, which might be blood. In accordance with additional embodiments, the fluid flow rate is additionally corrected for hemoglobin or hematocrit, and the effect of oxygen saturation on the hemoglobin or hematocrit data.

10 Claims, 10 Drawing Sheets

(51) Int. Cl.
    *A61B 8/00*     (2006.01)
    *A61B 5/145*     (2006.01)
    *G01F 1/00*     (2006.01)
    *A61B 8/06*     (2006.01)
    *A61B 5/01*     (2006.01)
    *A61B 5/026*     (2006.01)
    *A61M 1/14*     (2006.01)
    *A61M 39/28*     (2006.01)
    *G01F 1/66*     (2006.01)

(52) U.S. Cl.
    CPC ............ *A61B 5/14542* (2013.01); *A61B 8/06* (2013.01); *A61B 8/4477* (2013.01); *A61B 8/5223* (2013.01); *A61M 1/14* (2013.01); *A61M 1/3663* (2013.01); *A61M 39/281* (2013.01); *G01F 1/00* (2013.01); *G01F 1/66* (2013.01); *A61M 2205/3313* (2013.01); *A61M 2205/3334* (2013.01); *A61M 2205/3368* (2013.01); *A61M 2205/3375* (2013.01)

(56) References Cited

U.S. PATENT DOCUMENTS

| | | | |
|---|---|---|---|
| 5,474,683 A | 12/1995 | Bryant et al. | |
| 5,785,657 A | 7/1998 | Breyer et al. | |
| 5,856,622 A | 1/1999 | Yamamoto et al. | |
| 7,661,293 B2 | 2/2010 | Dam | |
| 7,661,294 B2 | 2/2010 | Dam | |
| 8,997,581 B2* | 4/2015 | Sato | G01F 1/667 73/861.18 |
| 9,638,557 B2* | 5/2017 | Takemura | G01F 1/66 |
| 2004/0191116 A1 | 9/2004 | Jarvik et al. | |
| 2005/0284815 A1 | 12/2005 | Sparks et al. | |
| 2007/0066928 A1 | 3/2007 | Lannoy | |
| 2008/0225925 A1 | 9/2008 | Laverdiere et al. | |
| 2009/0178490 A1 | 7/2009 | Konzelmann et al. | |
| 2010/0011416 A1 | 1/2010 | Wagner | |
| 2010/0110416 A1 | 5/2010 | Barrett et al. | |
| 2010/0143192 A1 | 6/2010 | Myrick et al. | |
| 2011/0009800 A1* | 1/2011 | Dam | A61M 1/3626 604/6.16 |
| 2011/0209558 A1 | 9/2011 | Sugiura et al. | |
| 2013/0305839 A1 | 11/2013 | Muench et al. | |
| 2014/0096599 A1* | 4/2014 | Munch | G01F 1/66 73/61.79 |

FOREIGN PATENT DOCUMENTS

| | | |
|---|---|---|
| JP | H09-511411 A | 11/1997 |
| JP | 2005-130969 A | 5/2005 |
| JP | 2013-195762 A | 9/2013 |
| WO | 2009042061 A2 | 4/2009 |
| WO | 2016138380 A1 | 9/2016 |

OTHER PUBLICATIONS

International Preliminary Report on Patentability of corresponding International Application No. PCT/US2016/019771 dated Aug. 29, 2017.
Poviliūnas, G. et al., Application of ultrasonic techniques for measurement of a flowrate of viscous liquids in a wide temperature range, Ultragarsas, 1999, 21-26, 3(33), Kaunas University of Technology, Kaunas, Lithuania.
Petkus, V. et al., Temperature dependence of a piezoceramic transducer electric impedance, Ultragarsas, 2005, 22-25, 3(56), Kaunas University of Technology, Kaunas, Lithuania.
Ahmed, Mawahib et al., Capacitor Device for Air Bubbles Monitoring, International Journal of Electrical & Computer Sciences, 2009, 12-15, vol. 9, No. 10, IJENS Publisher, Rawalpindi, Pakistan.
Perthel, Mathias et al., The dynamic bubble trap reduces microbubbles in extracorporeal circulation and high intensity transient signals in the middle cerebral artery: a case report, Perfusion, 2003, 325-329, 18, EBSCO Publishing.
Urbanek, Simon et al., Improved Methods for Measurement of Gaseous Microbubbles During Extracorporeal Circulation, downloaded from http://citeseerx.ist.psu.edu/viewdoc/download?doi=10.1.1.11.3316&rep=rep1&type=pdf on Jan. 23, 2018.
Extended European Search Report dated Sep. 28, 2018 which issued for corresponding EP Patent Application No. 16756444.2, 8 pages.
Hofmann, Friedrich, Fundamentals of Ultrasonic-flow Measurement for Industrial Applications, Krohne Messtechnik GmbH & Co. KG 2000, 31 pages.
Melexis Microelectronic Integrated Systems Data Sheet, Feb. 28, 2013, 52 pages.
Flow Measuring Technology for Liquids, Gases and Steam, Products and Services at a Glance, Endress + Hauser, at https://portal.endress.com/wa001/dla/5001109/7297/000/04/FA00005DEN_1918.pdf?gclid=EAIaIQobChMI65rJ-MnB4QlVw2SGCh3z3QrHEAAYASABEgl8QfD_BwE, downloaded Apr. 8, 2019, 64 pages.
Two Technologies for Flow Measurement from Outside a Pipe, Greyline Instruments Inc., 2 pages.
Japanese Office Action (with English translation) dated Dec. 24, 2019 during the prosecution of corresponding Japanese Patent Application No. 2017-545672, 12 pages.
Chinese Office Action and Chinese Search Report dated Oct. 31, 2019 during the prosecution of corresponding Chinese Patent Application No. 201680024270.3, 20 pages.

* cited by examiner

FLUID FLOW RATE MEASURING AND GAS BUBBLE DETECTING APPARATUS

This application is 371 national stage application in the United States of International Application No. PCT/US16/19771, which was filed on Feb. 26, 2016, and which claims priority to, and the benefit of, U.S. Provisional Application No. 62/121,674, filed Feb. 27, 2015. The disclosures of the above mentioned applications are hereby incorporated by reference in their entirety for all they disclose.

FIELD OF THE DISCLOSURE

The field of the present disclosure pertains to that of fluid flow rate sensing apparatuses and bubble detecting apparatuses, such as may be used to determine the flow rate of fluid in a tube or pipe, and which may be used to detect gas bubbles in the fluid in the tube or pipe. More specifically, the present disclosure pertains to fluid flow rate measuring and gas bubble detecting apparatuses, such as operate to both determine the flow rate of a fluid and to detect the presence or absence of bubbles in a fluid. The present disclosure further pertains to use of the aforementioned fluid flow rate measuring and gas bubble detecting apparatuses in one or more systems and medical procedures, including those relating to extracorporeal blood circuits and systems, more specifically cardiopulmonary systems and procedures involving the movement of blood to and/or from the heart via pumps replacing all or a portion of the pumping activity typical of a beating heart (e.g., cardiopulmonary bypass procedures), or also movement of blood in order to support/replace the function of the lung whereas the heart is not assisted (e.g. extracorporeal membrane oxygenation systems and procedures), or other applications where blood is moved (e.g., dialysis systems and procedures).

BACKGROUND OF THE DISCLOSURE

In the health field, medical equipment such as kidney dialysis machines, infusion pump blood analyzers, transfusion systems, cardio-pulmonary bypass/assist machines, and the like, include, or are attached to, tubes in which a patient's blood flows, or in which some form of infusion fluid flows. These fluids flow from these tubes into the patient's blood stream by means of a cannula, and it is important for patient care, and to ensure patient safety, that the flow rate of the fluid is appropriately monitored. It is also important to measure the temperature of these fluids entering the patient's body so as not to put undue stress on the patient with infusion of fluids that are substantially warmer or colder than target body temperatures, whether physiologic or therapeutic. In some cases, the infusion of fluids may have a fluid temperature that is substantially above, or substantially below, physiologic body temperature (e.g., therapeutic cooling during heart surgery to 18° C. followed by rewarming at the end of surgery). In such instances, the need to monitor temperature of the fluids in these cases is greater.

It is also important to monitor fluid flowing in these tubes for undesirably large gas bubbles, whether air or some other gas, because such gas bubbles have the potential to harm the patient as emboli when they enter the patient's bloodstream. One solution with respect to the monitoring of fluid flow rate, fluid temperature, and the monitoring for gas bubbles in the flowing fluid, is to provide separate sensors and associated electronic circuits for each of these parameters, namely, fluid flow rate, fluid temperature, and the presence of substantial gas bubbles. However, a disadvantage to such systems would be their complexity of construction, which makes them more costly to manufacture, deploy and maintain.

A partial solution to this problem is disclosed by U.S. Pat. No. 7,661,294 B2, issued to Dam, and which is incorporated herein by reference in its entirety. According to this Dam patent, a multi-function sensor system may be constructed with piezoelectric elements that are operated as part of an air bubble detection and characterization apparatus. Dam further discloses that the multi-function sensor system includes an infra-red thermocouple employed as a temperature sensor element operated to measure the internal temperature of liquid in a tube non-invasively by measuring both the tube surface temperature and ambient temperature. The multi-function sensor system disclosed by Dam includes a force/pressure sensor that accomplishes non-invasive measurement of internal pressure of an elastic tube to detect tube occlusion and/or disconnections.

The Dam patent discloses a liquid color sensing circuit that employs a light emitting element and phototransistor to sense the color of liquid in a tube. However, Dam does not disclose a circuit for detecting hematocrit and/or hemoglobin of blood in a tube. It is known that hematocrit and/or hemoglobin of blood may affect blood flow measurements, so there is a need for a blood flow sensing apparatus that senses blood flow rate more accurately in a tube or pipe by correcting for the effect of hematocrit/hemoglobin and/or the effect of temperature on the blood flow measurements.

There remains a need for a compact, easy to deploy and use apparatus that senses fluid flow rate and that detects the presence of gas bubbles for fluid flowing in a tube or pipe. Furthermore, there remains a need for an apparatus that senses fluid flow rate more accurately than previous fluid flow sensing apparatuses.

SUMMARY OF THE DISCLOSURE

An apparatus is disclosed herein that constitutes a fluid flow sensing and bubble detecting apparatus. In accordance with a non-limiting illustrative embodiment of such an apparatus, a fluid flow sensing and bubble detecting apparatus is described that includes (a) a housing provided with a channel configured to receive a tube through which fluid flows; (b) a sensor apparatus disposed within the housing, wherein the sensor apparatus includes a first sensor operable to measure a flow rate of a fluid, a second sensor operable to detect bubbles in a flowing fluid, and a temperature sensor operable to detect a temperature of a flowing fluid; and (c) a processor operably connected to receive fluid flow rate data obtained by the first sensor, and operably connected to receive bubble detection data obtained by the second sensor, and operably connected to receive fluid temperature data obtained by the temperature sensor. In accordance with this non-limiting embodiment of the apparatus, when a tube through which fluid is flowing is disposed in the channel of the housing, the first sensor measures the flow rate of the flowing fluid, and the second sensor detects bubbles in the flowing fluid, and the temperature sensor measures the temperature of the flowing fluid. In accordance with an embodiment of this disclosure, the fluid flow rate data, and the fluid temperature data may be used by the processor to calculate a temperature corrected fluid flow rate for the fluid flowing in the tube. Various other non-limiting illustrative embodiments of the apparatus are also disclosed herein.

A method is disclosed herein that constitutes a method of monitoring a fluid flowing through a tube that is a component of medical equipment or that is connected to medical equipment. Such a non-limiting illustrative embodiment of such a method comprises the steps of: (a) operating a fluid flow sensing and bubble detecting apparatus that comprises a sensor apparatus disposed within a housing in order to generate fluid flow rate data and fluid temperature data with respect fluid flowing within a tube or pipe, wherein the sensor apparatus includes a first sensor operable to measure a flow rate of a fluid, a second sensor operable to detect bubbles in the flowing fluid, and a temperature sensor operable to measure a temperature of the flowing fluid; and (b) calculating a temperature corrected fluid flow rate from the generated fluid flow rate data and the fluid temperature data, wherein calculation of the temperature corrected fluid flow rate is performed by a processor of the fluid flow sensing and bubble detecting apparatus. Various other non-limiting embodiments of the method are also disclosed herein.

DETAILED DESCRIPTION OF ILLUSTRATIVE, NON-LIMITING INVENTIVE EMBODIMENTS

Various illustrative, non-limiting embodiments of this disclosure are described as follows with reference to the drawings, in which like parts are designated with like character references. First, one or more non-limiting apparatus embodiments are described, and then one or more non-limiting method embodiments are described.

Figure 1:
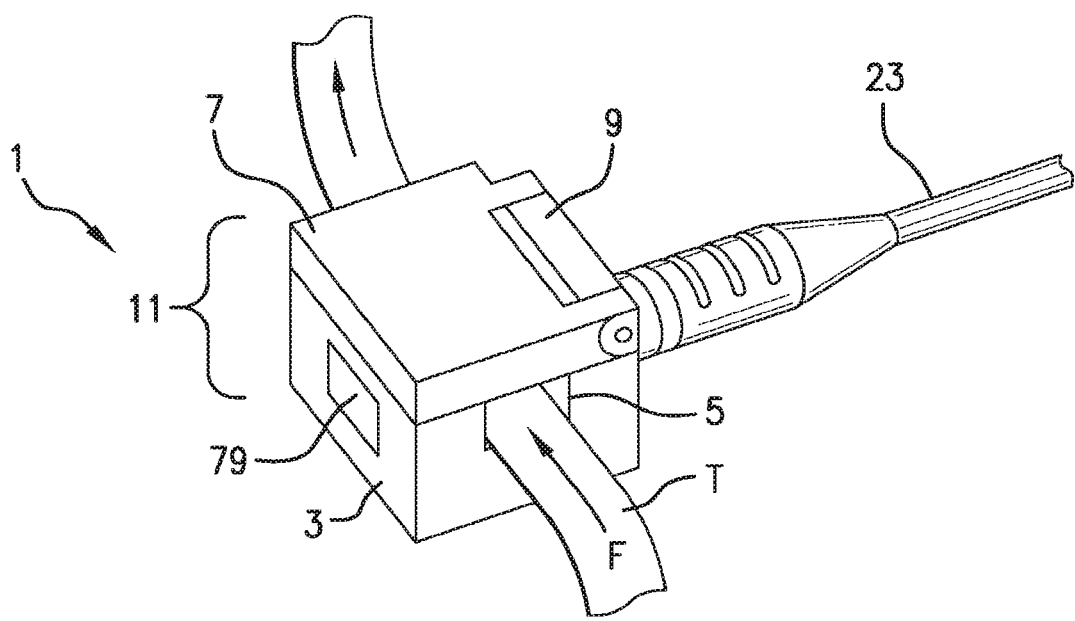
FIG. 1 is a perspective view of a fluid flow sensing and bubble detecting apparatus in accordance with a non-limiting illustrative inventive embodiment of this disclosure.

FIG. 1 illustrates a fluid flow sensing bubble detecting apparatus 1 that includes a main housing 3 provided with a channel 5 configured to receive a tube T through which fluid F flows. The tube T may be connected to medical equipment, such as a kidney dialysis machine, an infusion pump blood analyzer, a transfusion system, an extracorporeal membrane oxygenation (ECMO) machine, or a cardio-pulmonary bypass machine, or the tube T may be a component of a tubing set connected to such medical equipment. The fluid flowing in tube T may, thus, be blood; however, it may also be other kinds of physiologic fluids that include proteins, electrolytes, volume expanders, etc., which are fluids infusible into a patient. Furthermore, the fluid F flowing in the tube T may flow in either a forward or backward direction, and the fluid flow sensing and bubble detecting apparatus 1 is able to detect the direction of flow with its flow sensor. Thus, while some figures may show flow in the forward direction, the fluid flow sensing and bubble detecting apparatus 1 is capable of detecting fluid flow in the reverse direction.

The tube T is preferably clear and/or translucent, and may be constructed from medical grade tubing such as PVC, silicone, polycarbonate, or other types of medical grade tubing. The apparatus 1 may be provided with a cover 7 that is connected by a hinge 9 or other fastener to the main housing 3 so as to form a clam-shell housing 11 that securely fixes the tube T in the channel 5. Because the apparatus 1 has a clam-shell housing 11 that clamps onto the tube T, the apparatus may be characterized as an external clamp-on sensor system that clamps onto the exterior of tube T.

Figure 2:
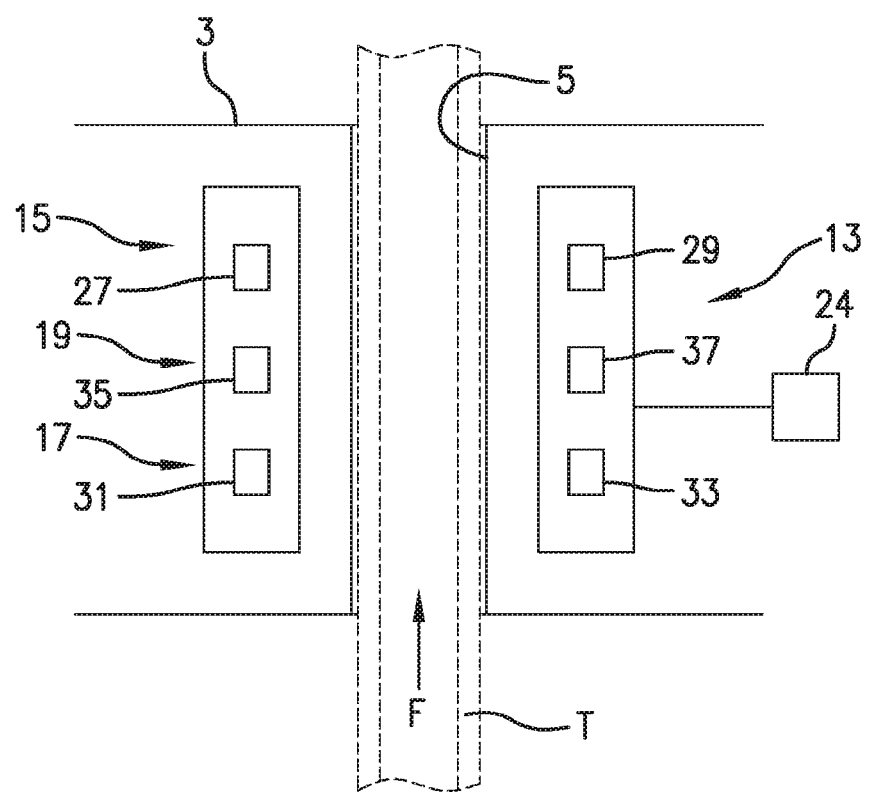
FIG. 2 is a schematic illustration of a sensor apparatus of the fluid flow sensing and bubble detecting apparatus of FIG. 1.

Disposed within the main housing 3 is a sensor apparatus 13, as shown in FIG. 2, that includes a first sensor 15 positioned, and operable, so as to measure or sense a flow rate of the fluid F flowing in the tube T, and a second sensor 17 positioned, and operable, to detect bubbles in the flowing fluid F, and a temperature sensor 19 positioned, and operable, so as to measure or sense the temperature of the flowing fluid F. Thus, when tube T through which fluid F is flowing is disposed in the channel 5 of the main housing 3, the first sensor 15 measures the flow rate of the flowing fluid, and the second sensor 17 detects bubbles in the flowing fluid, and the temperature sensor 19 measures the temperature of the flowing fluid. The temperature sensor 19 is capable of measuring the temperature of the fluid whether it is flowing or standing still (i.e., no flow). The first sensor 15 is a flow sensor that can detect a no flow state, as well as detect flow in either direction. The second sensor 17 is a bubble detection sensor and can only detect a bubble if the bubble is moving at a certain minimum speed and has a certain minimum size, although it is not necessary for the fluid to flow for the second sensor 17 to detect bubbles moving in the fluid F.

Because the sensor apparatus 13 includes an array of sensors 15, 17 and 19, the sensor apparatus 13 may also be characterized as a sensor array. Optionally, the sensor array may include a sensor for measuring ambient temperature in addition to, or instead of, the fluid temperature measured by temperature sensor 19. In other words, an ambient temperature sensor may be employed to provide data used to compensate for ambient temperature effects on the flowing fluid temperature measurement obtained by the temperature sensor 19. In addition, the location and characteristics of temperature sensor 19 permit it to measure temperature changes reflecting a steady state more quickly (e.g., on the order of seconds to less than one minute) with respect to fluid F in tube T than in prior art devices in which the steady state following a temperature change may take up to an hour to reach equilibrium as a result of affects caused by the housing of such devices.

Figure 3:
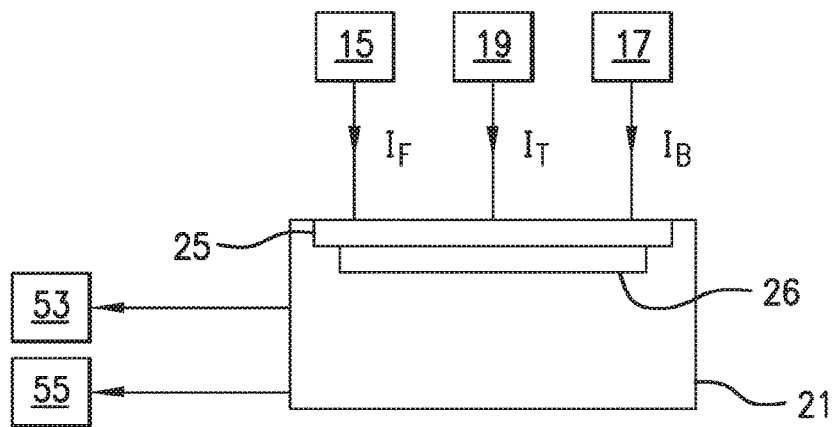
FIG. 3 is a schematic illustration of a processor employed to receive data from sensors of the sensor apparatus of FIG. 2.

The apparatus 1 may further include a processor 21 connected to receive fluid flow rate data signal(s) $I_F$ provided by the first sensor 15, and connected to receive bubble detection data signal(s) $I_B$ provided by the second sensor 17, and connected to receive fluid temperature data signal(s) $I_T$ provided by the temperature sensor 19, as illustrated schematically in FIG. 3. The processor may be located within the main housing 3, or the clam-shell housing 11, or the processor may be located remotely from the sensor array and in its own separate housing. In the case when the processor 21 is located remotely from the sensor array, a transmission cable 23 is attached to the main housing 3 and provides a transmission path between the sensor array 13 and the processor 21 over which the data signals $I_F$, $I_B$, $I_T$ are transmitted from sensor array 13 to processor 21. Alternatively, the sensor array 13 may be connected to a transmitter 24 that is able to transmit the data signals $I_F$, $I_B$, $I_T$ wirelessly (e.g., via GSM, Bluetooth, WLAN, etc.) to a receiver 25 that is either a part of the processor 21, or operatively connected to the processor 21. The processor 21 may also be provided with a signal processing circuit 26 that processes the signals $I_F$, $I_B$, $I_T$ and outputs processed input to the processor 21. Details of the signal processing circuit 26 are provided further below in this disclosure.

The processor 21 uses the fluid flow rate data obtained by the first sensor 15 to calculate the fluid flow rate Q of the fluid F in the tube T. However, the processor 21 also uses the temperature data obtained by the temperature sensor 19 to correct the calculated fluid flow rate for temperature of the fluid. By correcting the calculated fluid flow rate for the temperature of the fluid F, the calculated flow rate will be substantially more accurate than calculated fluid flow rates not corrected for the temperature of the fluid F. Thus, the processor 21 employs the fluid flow rate data and the temperature data for the fluid F together to calculate a temperature corrected fluid flow rate $Q_{TC}$ that is desirably more accurate than fluid flow rate computed without correcting for the temperature of the fluid F. The fact that temperature of a fluid F may have a substantial effect on flow measurements of the fluid is a known phenomenon as disclosed by G. Poviliunas et al., Application of Ultrasonic Techniques for Measurement of a Flowrate of Viscous Liquids in a Wide Temperature Range, 3 ULTRAGARSAS 1392-2144 (1999), at http://www.ktu.lt/ultra/journal/pdf_33_3/33-1999-vol.3_04-g.poviliunas.pdf.

Without being limited to a particular theory, the calculation of the flow rate of a fluid is dependent upon its density, which is known to change with temperature. As an alternative theory, or in addition thereto, temperature influences the speed of ultrasonic signals traveling in the flowing fluid, which are used to measure flow rates. Therefore, varying temperature of a fluid introduces error into flow meter measurements of fluid flow. However, temperature correction factors for flowing fluids are known and/or are ascertainable without undue experimentation. In accordance with the apparatus and method embodiments described herein, temperature correction of calculated fluid flow rate may be achieved using a propagation time difference method corrected for temperature, such as disclosed by U.S. Patent Application Publication No. US 2011/0209558 A1 and U.S. Patent Application Publication No. US 2009/0178490 A1 which are both incorporated herein by reference for all they disclose. Thus, the flowmeter sensor 15 may be characterized as a transit time flowmeter. However, it is within the scope of this disclosure to employ other suitable models for calculating fluid flow from one or more ultrasonic signals transmitted through the flowing fluid.

The first sensor 15 that measures fluid flow and generates fluid flow rate data signal(s) $I_F$ received by the processor 21 may be embodied as an ultrasonic flowmeter. In accordance with a non-limiting embodiment of the first sensor 15, the ultrasonic flowmeter includes an ultrasonic pulse emitter-receiver 27, and an ultrasonic pulse emitter-receiver 29 that is disposed either upstream or downstream to receive ultrasonic pulses emitted from the ultrasonic pulse emitter 27, and vice-versa, so that ultrasonic pulses that have traveled transversely at an acute or obtuse angle through the flowing fluid are used by the first sensor 15 to generate, in a known manner that requires upstream and downstream travel time in order to calculate a time difference that is then used for flow calculation, fluid flow rate data corresponding to the fluid flow rate of the flowing fluid. The components 27 and 29 of the first sensor 15 may be constructed as piezoelectric elements of any suitable material, such as lead zirconate titanate (PZT), or modified PZT, or lead-free piezo ceramics, or polyvinylidene difluoride (PVDF) materials. Also, each of the piezoelectric elements 27, 29 are ultrasonic transducers capable of both emitting and receiving ultrasonic signals so that the piezoelectric elements 27, 29 may each generate fluid flow rate data while transmitting and receiving in a reciprocal manner with each other, such as described in U.S. Patent Application Publication No. US 2009/0178490 A1 and in U.S. Patent Application No. US 2011/0209558 A1, which are incorporated herein by reference, in order to generate fluid flow rate data signal(s) $I_F$.

The second sensor 17 that detects bubbles in the flowing fluid and generates bubble detection data signal(s) $I_B$ received by the processor 21 may be embodied as an ultrasonic detector. In accordance with a non-limiting embodiment of the second sensor 17, the second sensor 17 includes an ultrasonic pulse emitter 31, and an ultrasonic pulse receiver 33 that is disposed to receive ultrasonic pulses emitted from the ultrasonic pulse emitter 31, so that ultrasonic pulses that have traveled through the flowing fluid are used by the second sensor 17 to generate bubble detection data corresponding to the presence, and/or absence, of bubbles in the flowing fluid. The components 31 and 33 of the second sensor 17 may be constructed as piezoelectric elements of any suitable material, such as lead zirconate titanate (PZT), or modified PZT, or lead-free piezo ceramics, or polyvinylidene difluoride (PVDF) materials, such as disclosed by U.S. Pat. No. 7,661,294 B2, which is incorporated herein by reference. Also, each of the piezoelectric elements 31, 33 may each be ultrasonic transducers capable of both emitting and receiving ultrasonic signals so that the piezoelectric elements 31, 33 may generate bubble detection data while transmitting and receiving in a reciprocal manner with each other in order to generate bubble detection data signal(s) $I_B$.

The temperature sensor 19 that detects temperature of the flowing fluid and generates fluid temperature data signal(s) $I_T$ received by the processor 21 may be embodied as a non-invasive, non-contact infra-red detector (i.e., an infra-red thermometer, such as Melexis MLX90614 or MLX81101) that measures temperature of flowing fluid with an accuracy of about ±0.5° C., depending on the type of tube T employed. For example, when the tube T is made of polycarbonate, the non-invasive infra-red detector (Melexis MLX90614 sensor) measures temperature of the flowing fluid with an accuracy of ±0.5° C. with ambient temperature compensation. However, deploying other kinds of tubing T, such as silicone tubing, may affect the accuracy of the infra-red detector so that the temperature measurements may be less accurate.

Figure 4:
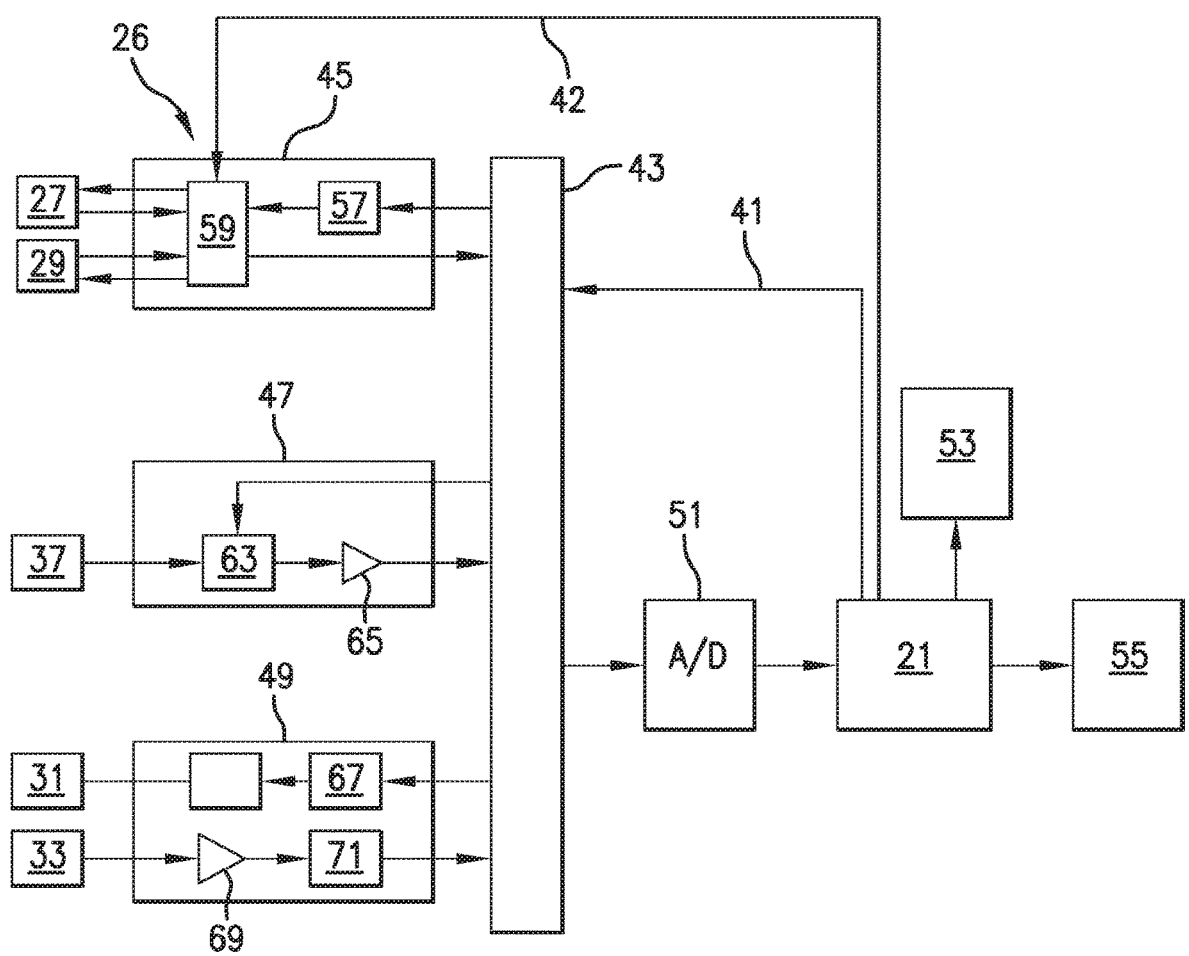
FIG. 4 is a schematic illustration of the electronics of a non-limiting illustrative inventive embodiment of a fluid flow sensing and bubble detecting apparatus of this disclosure.

The temperature sensor 19 is preferably an infra-red sensor that has no direct contact with the fluid F, for example blood, flowing in the tube T. In accordance with another non-limiting embodiment of the temperature sensor 19, the temperature sensor 19 may constitute a thermocouple assembly that involves a light emitting element 35, such as a infra-red light emitting diode (LED), and a light receiving element 37, such as a silicon photo transistor, which is disposed to receive infrared light emitted from the light emitting element 35. In this alternate embodiment of a non-contact sensor 19, infrared light generated by the LED that has traveled through the flowing fluid is used by the temperature sensor 19 to generate analog fluid temperature data corresponding to the temperature of the flowing fluid. It is preferable, however, to embody the temperature sensor 19 as a single, passive infra-red (IR) thermometer detector instead of as an LED 35 and light receiving element 37 combination because the single infra-red thermometer detector is a passive sensor that detects IR radiation emitted by the fluid F. Consequently, the infra-red thermometer detector is disposed only on one side of the tube T, does not emit any light, and employs IR radiation entering the sensor from the tube T to warm a membrane of the infra-red thermometer detector. The temperature of this membrane is measured and compared to other internal temperatures One non-limiting example of the signal processing circuit is shown in FIG. 4. The processor 21, which may be a microprocessor, is suitably programmed to perform all of the functions described below. That is, the processor 21 outputs the necessary signals to control the operation of each of the several sensor elements to perform its intended function and to produce an output measurement. The processor 21 also has an output on line 41 that controls operation of a bi-directional multiplexer 43 that is gated by the processor 21 to sequentially apply the signals from the processor 21 to control operation of a fluid flow rate measuring circuit 45 associated with offset piezoelectric sensor elements 27 and 29, a temperature measuring circuit 47 associated with infrared sensor element 37 (or, alternatively, with an IR thermometer detector such as a Melexis MLX90614 sensor), and an air bubble detection circuit 49 associated with the piezoelectric sensor elements 31 and 33. The piezoelectric sensor elements 31 and 33 of the air bubble detection circuit 49 may be, but do not have to be, offset in a manner such as described with respect to piezoelectric sensor elements 27 and 29. In other words, piezoelectric sensor elements 27 and 29 may be located directly across from one another when tube T is disposed in channel 5 of the housing 3.

An analog to digital converter 51 digitizes analog output signal(s) from any of the circuits 45, 47 and 49 and applies it to the processor 21 for processing for producing the proper output depending upon the sensor element that is active. The processor 21 is operably connected to drive an audio-visual display apparatus 53 to display measurement results, warnings, and other information, in either solely visual mode, solely audio mode, or in a combined audio and visual mode. The processor also can produce outputs to other devices 55 such as printers, audio alarms, vibratory alarms, record recording devices, etc.

The fluid flow rate measuring circuit 45 is gated on for operation by the multiplexer 43 for a predetermined time by the processor 21. Energy in the ultrasonic frequency range, e.g., 2-5 MHz, is supplied by the generator 57 to ultrasonic sensor element 27 (or 29) that is to be the transmitter element to be transmitting to the opposing other ultrasonic sensor element 29 (or 27) serving as the receiver element, and then vice versa. Electronics 59 includes a multiplexer and may be provided with a timer counter, such as disclosed by FIG. 2 of U.S. Pat. No. 5,856,622, which is incorporated herein by reference in its entirety, in order to direct sequential transmission and reception of ultrasonic wave signals between ultrasonic sensor elements 27, 29 based on a clock signal. Electronics 59 receives control signals directly from the processor 21 via line 42. Received ultrasonic energy is converted by the piezoelectric sensor elements. The signal is then processed by electronics 59 to an analog output voltage that correlates with the time difference of the ultrasonic signal in and against flow direction. The analog output, which may be optionally amplified by an amplifier (not shown) if needed, is applied to the analog digital (A/D) converter 51, and the digital output is input as fluid flow rate data to processor 21 for processing with fluid temperature data, and then displayed via display apparatus 53 as temperature corrected fluid flow rate $Q_{TC}$ of the flowing fluid F.

The temperature measuring circuit 47 is any suitable conventional circuit used to measure temperature based on infrared (IR) energy. Such circuits are well known in the art. When gated on by the processor 21 through the multiplexer 43, electronics 63 of the temperature measuring circuit 47 produce an analog output voltage that is amplified by an amplifier 65. The amplified analog output is applied to the analog to digital (A/D) converter 51, and the digital output is input as fluid temperature data to the processor 21 for processing with fluid flow rate data as discussed above, and optionally displayed via display apparatus 53 as fluid temperature of the flowing fluid F.

In an embodiment of this disclosure, an IR thermometer detector, such as a Melexis MLX90614 sensor, may be employed as temperature sensor 19 instead of the LED 35 and light receiving element 37 assembly. In this embodiment, the IR thermometer (Melexis MLX90614) may input an analog PWM signal to the electronics 63 of the temperature measuring circuit 47. However, the Melexis MLX90614 sensor is provided with its own digital interface (SMBus/ "I2C"), so its input into the processor 21 may be digital, in which case there can be a direct connection between the Melexis MLX90614 sensor and the processor (not gated via the multiplexer). On the other hand, it is also possible to connect the digital output of the Melexis MLX90614 sensor to the multiplexer 43 using a digital-to-analog converter incorporated in the electronics 63, which would allow the electronics 63 to accept a digital input instead of an analog input.

The air bubble detection circuit 49 is also gated on for operation by the multiplexer 43 for a predetermined time by the processor 21. Energy in the ultrasonic frequency range, e.g. 2-5 MHz, is supplied by a generator 67 to ultrasonic sensor element 31 (or 33) that is to be the transmitter element transmitting to the opposing other element 33 (or 31) that is to be serving as the receiver element. The received ultrasonic energy is amplified in an amplifier 69 and detected and preferably split by a suitable circuit 71 into a steady state (DC) component and a varying or transient (AC) component, wherein the components respectively are indicative of the absence and the presence of an air bubble or a particle in the liquid, as described in U.S. Pat. No. 7,661,293 B2, which is incorporated herein by reference in its entirety. The two components of the signal are applied to the A/D converter 51 whose output is supplied to microprocessor 21, which uses the digital data that corresponds to the presence of a varying transient component to indicate the presence of an air bubble (and/or a particle as well) and to determine its characteristics. The component signals may be modified to adjust the sensitivity of bubble detection so that thresholds with respect to bubble size may be selectively set. In particular, it is advantageous to provide a gated control of the air bubble detection circuit 49 using the multiplexer 43 to selectively set at least three threshold limits for bubble size detection. When liquid is flowing through the tube T, the presence of the steady-state component of the split signal indicates that the system is operating properly to provide a continuous self-check against system malfunction.

The air bubble detection circuit 49 of this disclosure is just one example of a suitable air bubble detection circuit. Other circuits suitable for air bubble detection may be employed in the electronics of a fluid flow rate measuring and gas bubble detecting apparatus in accordance with this disclosure, such as in those apparatuses schematically illustrated by FIGS. 4, 5, 7, 9, 10 and 11. In this context, detected bubble size pertains to a cross sectional area of the tube rather than the volume of the bubble. However, because multiple piezoelectric sensors in accordance with some embodiments of the sensor array may detect bubbles along substantially different pathways, and because fluid flow rate is measured, bubble detection size may pertain to an estimated volume of a bubble. This improves bubble detection accuracy by the processor, which can use both bubble detection data, and bubble flow rate data, to detect bubbles. In accordance with this disclosure, the air bubble detection circuit 29 may be constructed to operate based on an "amplitude drop method," which sends frequent pulses in order to monitor continuously the fluid to determine whether bubbles are present or not. According to the amplitude drop method, when there is a certain threshold drop of the received amplitude of the pulses that are sent frequently between the piezoelectric sensors, then the circuit construes this threshold drop as a detected bubble, and a bubble alarm is activated. In this way, a bubble cannot pass through the fluid flow rate measuring and gas bubble detecting apparatus without being detected. Consequently, even if the tube T becomes totally filled with air instead of a fluid F, the bubble alarm gets triggered because the received amplitude of the pulses emitted by the piezoelectric sensors falls below the minimum threshold. Thus, an air bubble detection circuit 49 constructed to operate based on the amplitude drop method continuously monitors the tube T to detect whether there is a bubble present or not in the flowing fluid F and it detects whether the tube T is completely or almost completely filled with air, which is a condition that might fool other bubble detection circuits.

Figure 5:
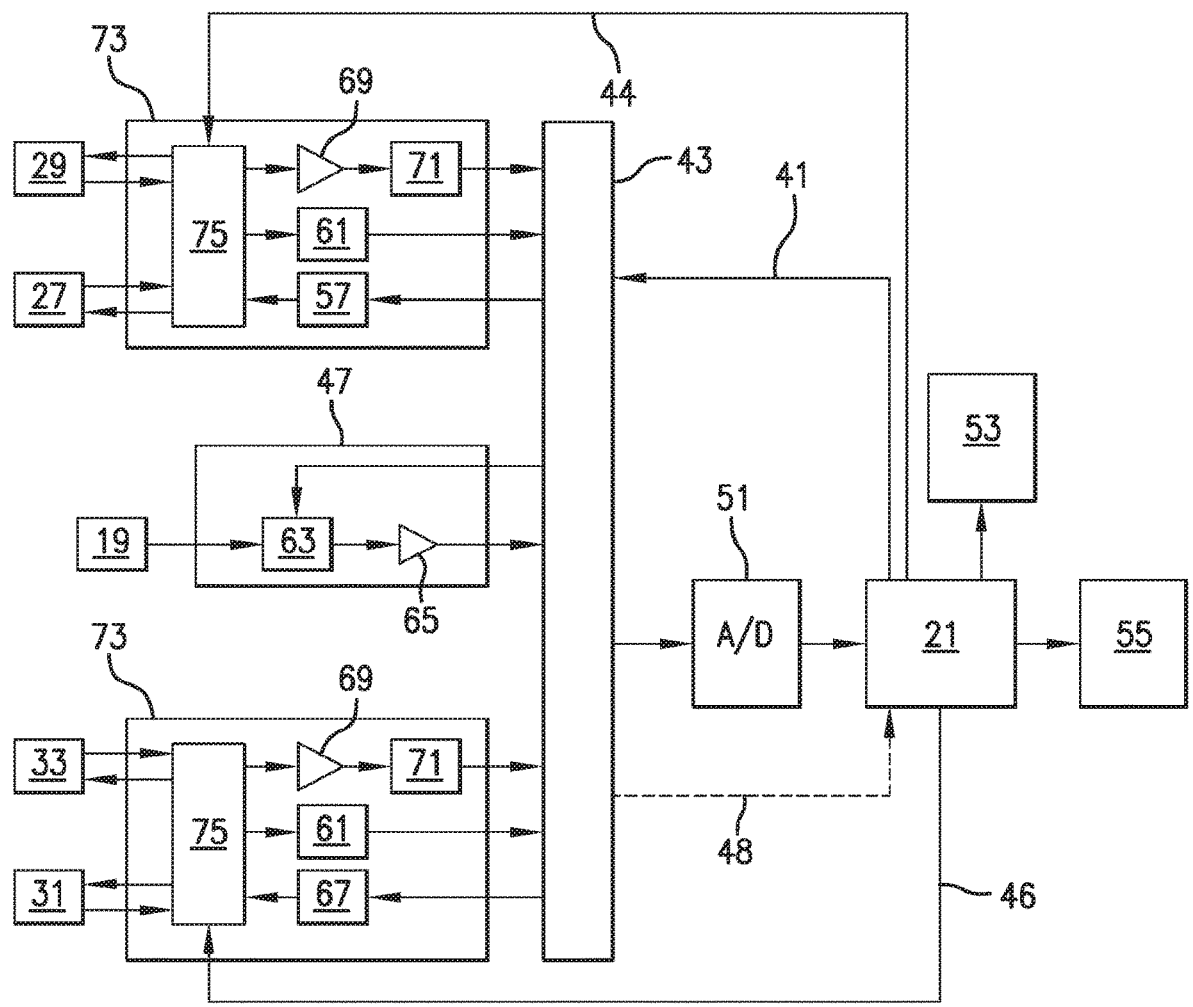
FIG. 5 is a schematic illustration of the electronics of another non-limiting illustrative inventive embodiment of a fluid flow sensing and bubble detecting apparatus of this disclosure.

Because the sensors 27, 29, 31 and 33 of the fluid flow rate measuring circuit 45 and the air bubble detection circuit 49 are ultrasonic piezoelectric sensors, it is possible to employ them for double duty as both fluid flow rate detection sensors and fluid bubble detection sensors. As shown in FIG. 5, the circuit of FIG. 4 may be modified to replace circuits 45 and 49, respectively, with dual fluid flow rate and bubble detection circuits 73, which include a multiplexing circuit 75 for multiplexing the data input signals from ultrasonic sensors 27 and 29 (or 31 and 33). The multiplexed signals then are used for fluid flow rate measurement using the appropriate fluid flow rate data processing electronics 61 (which may include a timing circuit, a timing counter, amplifier, etc.), or for fluid bubble detection using the appropriate bubble detection data electronics 69 and 71. In this way, the accuracy of fluid flow rate measurement and of bubble detection is improved because two separate ultrasonic pulse paths are used to generate data regarding fluid flow rate and the presence (or absence) of bubbles in the fluid. Furthermore, the ultrasound signal generators 57, 67 of FIG. 5 may be embodied as a single generator gated by the multiplexer 43 to supply energy for the sensor elements of both dual fluid flow rate and bubble detection circuits 73. Multiplexer 75 can direct the electronic signal from the generator connected to it to any of the piezoelectric sensor elements operably connected to the multiplexer 75. Control of the multiplexer 75, including its timed gating operation, is provided by the processor 21. In accordance with another embodiment of this disclosure, the multiplexer 75 may incorporate a timing circuit, such as disclosed by FIG. 2 of U.S. Pat. No. 5,856,622, which is incorporated herein by reference in its entirety.

Figure 6A:
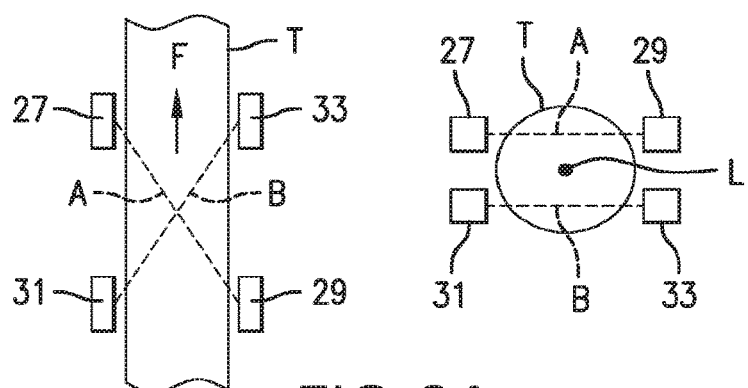
FIGS. 6A and 6D are schematic illustrations of ultrasonic piezoelectric sensor orientations about a tube or pipe T in accordance with illustrative and non-limiting inventive embodiments of this disclosure.
Figure 6B:
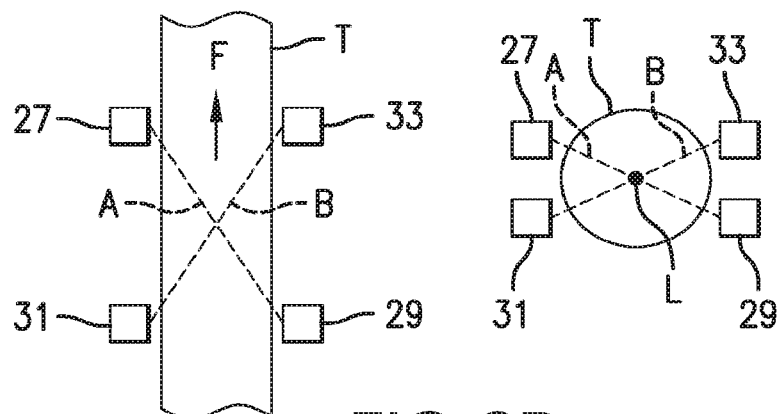
FIG. 6B is a schematic illustration of ultrasonic piezoelectric sensor orientation about a tube or pipe T in accordance with another non-limiting inventive embodiment of this disclosure.
Figure 6C:
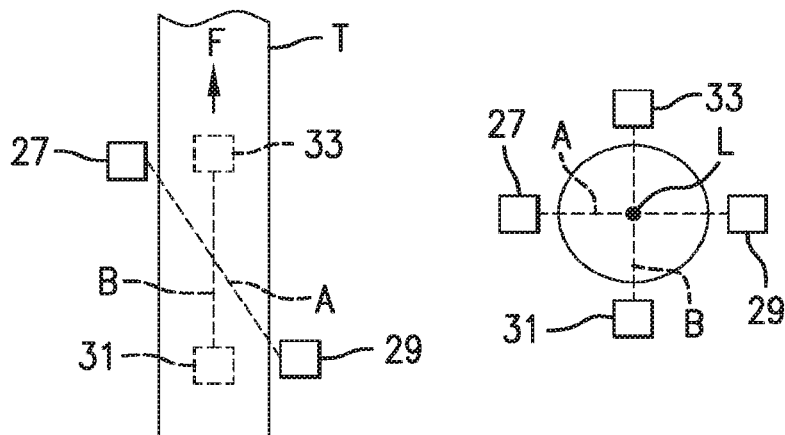
FIG. 6C is a schematic illustration of ultrasonic piezoelectric sensor orientation about a tube or pipe T in accordance with another non-limiting inventive embodiment of this disclosure.
Figure 6D:
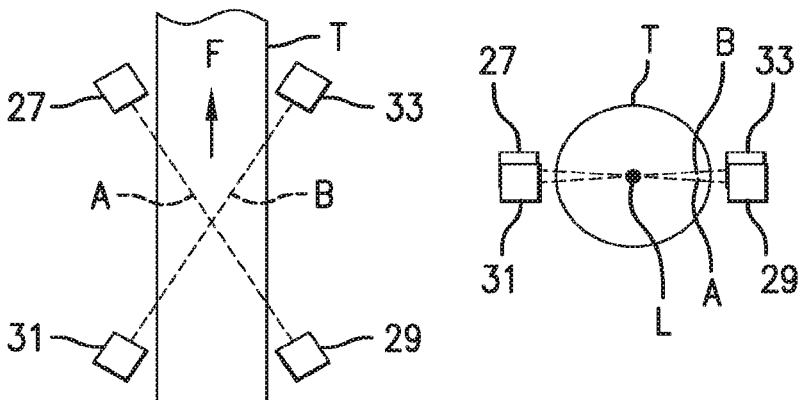

As shown in FIGS. 6A and 6B and 6C and 6D, the ultrasonic flow path A between sensors 27 and 29, and the ultrasonic flow path B between sensors 31 and 33, may be located at different height levels spaced lengthwise along the tube T (FIG. 6A) or at different crisscrossing levels spaced lengthwise along the tube T (FIG. 6B), or at top-bottom and left-right orientations (FIG. 6C) to form a cross, or at the same height level spaced lengthwise along the tube T (FIG. 6D). As evident from FIGS. 6A, 6B, 6C and 6D, the ultrasonic sensors 27 and 29, and 31 and 33, are paired together so as to send and receive ultrasonic signals back and forth along paths A and B, respectively, in a manner that is transverse to fluid flow F.

In the embodiment of FIG. 5, temperature data regarding fluid F may be provided to the circuit of FIG. 5 by a light receiving element 37 as shown in FIG. 4, which is an IR thermocouple generating analog output. Such analog output must be processed by the A/D converter 51 before it is input into processor 21. However, alternatively, the temperature data regarding the fluid F is preferably provided by an IR thermometer detector, such as a Melexis MLX90614 sensor, which generates digital output. Such digital output may be input via line 48 to the processor 21 without processing by the A/D converter 51 or by any other A/D converting circuitry.

Figure 7:
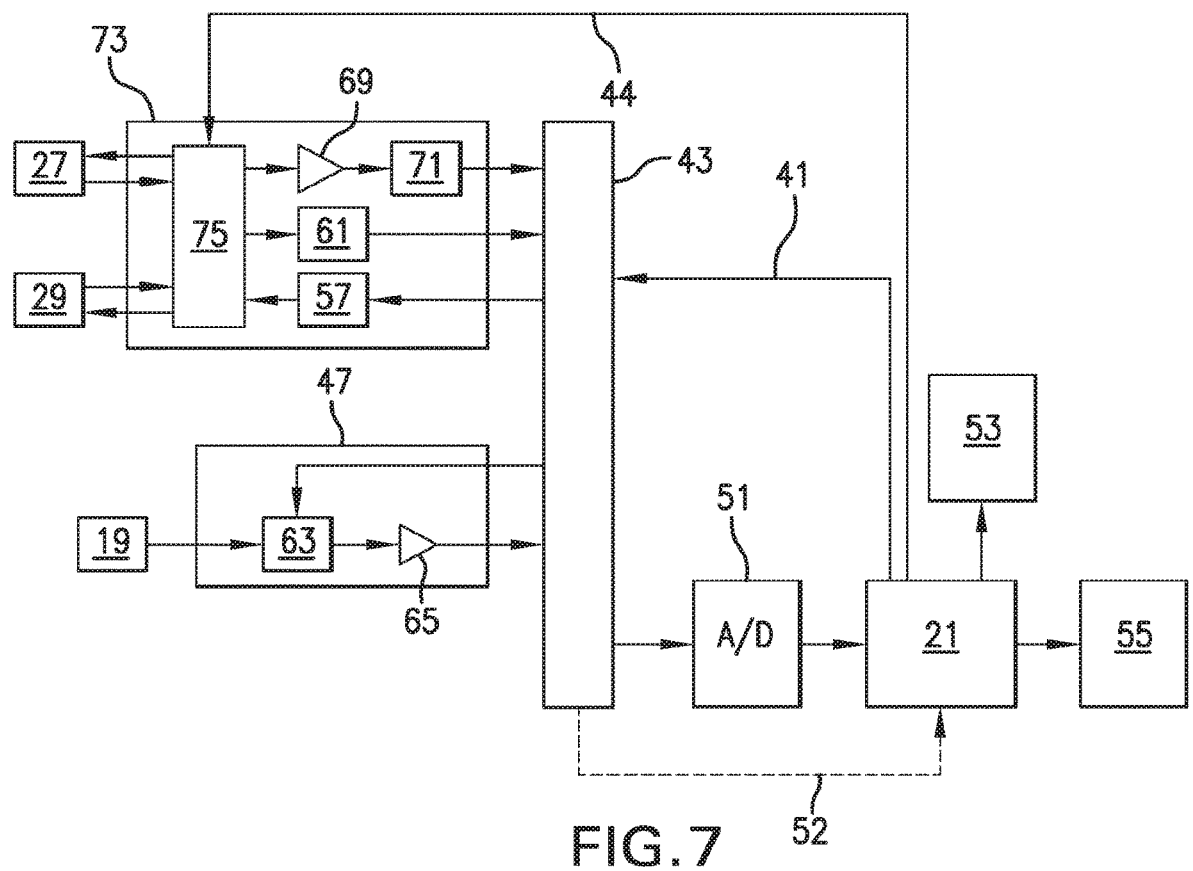
FIG. 7 is a schematic illustration of the electronics of another non-limiting illustrative inventive embodiment of a fluid flow sensing and bubble detecting apparatus of this disclosure.

In accordance with another non-limiting embodiment, as shown in FIG. 7, only one pair of sensors 27, 29 is required to effect both fluid flow rate measurement and fluid bubble detection. In this case, the sensors 27, 29 are located so that the ultrasonic pulse path between the paired sensors is oriented either horizontally or vertically with respect to the cross-section of the tube T, and transversely bisects the cross-section of tube T though the center longitudinal axis L of tube T at either an acute or an obtuse angle. In other words, there must be a non-orthogonal angle between the direction of fluid flow and the path of the transmitted ultrasound signals. In this embodiment, the measurement accuracy of fluid flow rate and the detection accuracy of fluid bubbles may be less than that of the embodiment of FIG. 5; however, fewer ultrasonic piezoelectric sensors are required, which decreases construction costs and permits the construction of a more compact, space-saving fluid flow sensing and bubble detecting apparatus. If the temperature sensor 19 is an analog sensor, such as an IR temperature sensor, then its output can be processed by the A/D converter 51. If the temperature sensor 19 is a digital sensor, such as a Melexis MLX90614 sensor, then the digital output may be input to the processor 21 via line 52.

Figure 9:
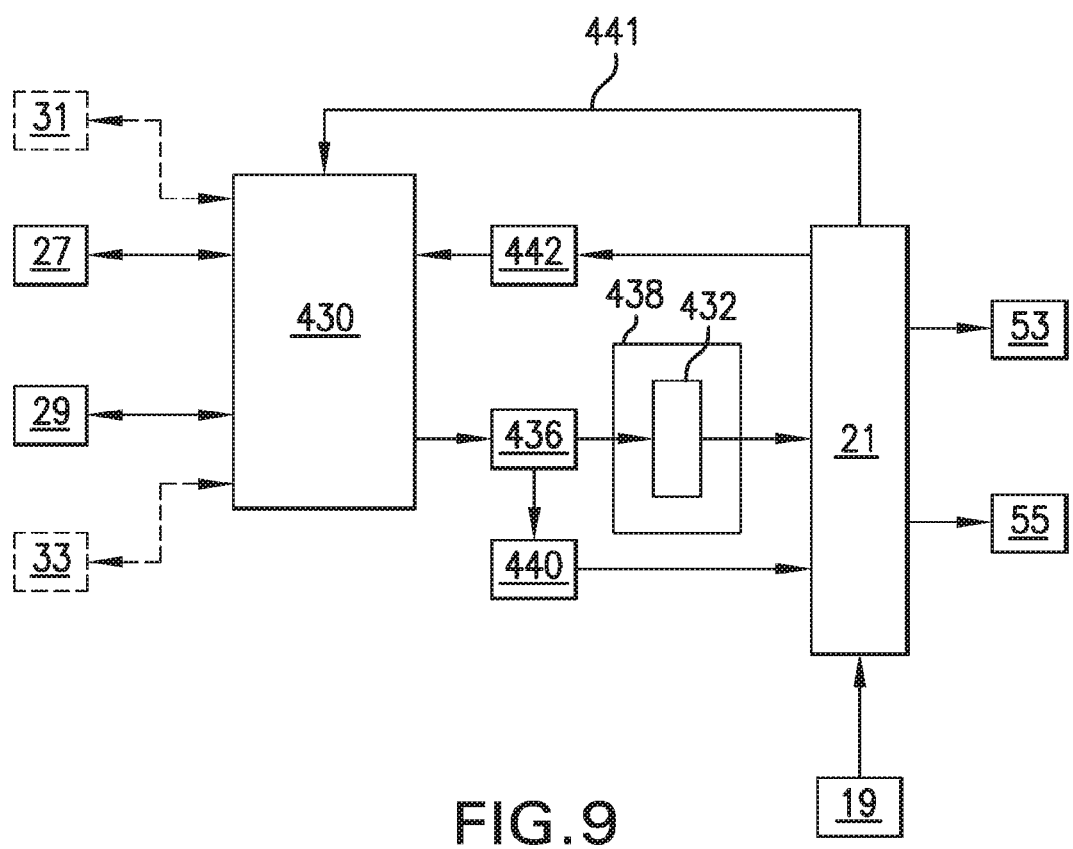
FIG. 9 is a schematic illustration of the electronics of another non-limiting illustrative inventive embodiment of a fluid flow sensing and bubble detecting apparatus of this disclosure.

FIG. 9 schematically illustrates another embodiment of a fluid flow sensing and bubble detecting apparatus in accordance with this disclosure. According to the embodiment of FIG. 9, paired piezoelectric sensors 27, 29 are operably connected to provide sensor input and output to a multiplexing circuit 430, which is connected to provide input, after amplification by an amplifier 436, to a timing circuit 432 of an electronics circuit 438. The timing circuit 432 comprises a time counter as described with respect to FIG. 2 of U.S. Pat. No. 5,856,622, and the timing circuit 432 provides digital input to the processor 21 that is used for controlling a time interval between the ultrasonic wave transmission from one of the paired sensors 27, 29 and the ultrasonic wave reception by the other one of the paired sensors 27, 29, and vice versa. Optionally, a second pair of ultrasonic sensors 31, 33 may be operably connected to provide sensor input and output as well to the multiplexing circuit 430 in order to determine fluid flow rates. In this case, the timing circuit 432 provides digital input to the processor 21 that is used for controlling a time interval between the ultrasonic wave transmission from one of the paired sensors 31, 33 and the ultrasonic wave reception by the other one of the paired sensors 31, 33, and vice versa, and that is also used for gating activation of each sensor pair 27, 29 and 31, 33 at different times. A temperature sensor 19, such as a Melexis MLX90614 sensor described above, inputs digital temperature data pertaining to the fluid flowing in the tube T into the processor 21.

Output from the multiplexing circuit 430 is amplified by an amplifier 436, and then input into the electronics circuit 438 before a signal processed by electronics circuit 438 is input into the processor 21 in order to determine fluid flow rate of the fluid in the tube T. However, amplified signal from amplifier 436 may also be input into a suitable circuit 440 that splits the signal into a steady state (DC) component and a varying or transient (AC) component, wherein the components respectively are indicative of the absence and the presence of an air bubble or a particle in the liquid, as described in U.S. Pat. No. 7,661,293 B2, which is incorporated herein by reference in its entirety. The two components of the signal are applied to an A/D converter that is incorporated in the suitable circuit 440 before becoming output supplied to microprocessor 21, which uses the inputted signal data to indicate the presence of an air bubble (and/or a particle as well) and to determine its characteristics.

The processor 21 outputs calculated fluid flow rate data, which may be corrected for temperature of the fluid, and calculated bubble detection data, to audio-visual display apparatus 53 and to other devices 55. Processor 21 also has an output on line 441 that controls operation of the bi-directional multiplexer 430 that is gated by the processor 21 to sequentially apply the signals from the processor 21 to control operation of the piezoelectric sensor elements 27 and 29 (and 31 and 33, when present) when operating these sensors to determine fluid flow rate data and to detect the presence of air bubbles and/or particles. Processor 21 also controls energy in the ultrasonic frequency range, e.g., 2-5 MHz, supplied by the ultrasound generator 442 to ultrasonic sensor element 27 (or 29) that is to be the transmitter element to be transmitting to the opposing other ultrasonic sensor element 29 (or 27) serving as the receiver element, and then vice versa. When multiple pairs of ultrasonic sensor elements are employed, such as paired sensors 27, 29 and paired sensors 31, 33, the processor controls the energy supplied to one sensor 27, 31 of each pair so that it acts as an ultrasound transmitter while the other member 29, 33 of the pair acts as a receiver, and then the processor controls the energy supplied so the other member 29, 33 of each pair so it serves as the transmitter while the sensor 27, 31 of each pair behaves as the receiver.

Because there is only one timer circuit 432, when multiple pairs of ultrasonic elements are employed only one sensor pair is activated at a time to collect fluid flow rate data or bubble detection data. For example, using the multiplexer 430, first the sensors 27 and 29 are activated so that sensor 27 serves as emitter and sensor 29 serves as receiver, then the multiplexer activates sensors 27 and 29 so that sensor 29 serves as emitter and sensor 27 serves as receiver, so that fluid flow rate data is obtained. While sensors 27 and 29 are activated, sensors 31 and 33 are not activated. Subsequently, the multiplexer 430 activates sensors 31 and 33, which means that sensors 27 and 29 are not activated, so that sensor 31 serves as emitter and sensor 33 serves as receiver in order to obtain fluid flow rate data. Subsequently, multiplexer 430 activates sensor 33 so that it serves as emitter and sensor 31 serves as receiver in order to obtain fluid flow rate data. Afterwards, the multiplexer may activate sensors 31 and 33 in order to collect bubble detection data, while the sensors 27 and 29 are inactive, and subsequently activate sensors 27 and 29 in order to collect bubble detection data while sensors 31 and 33 are inactive. Bubble detection data may be generated when emitting a signal only in one direction, e.g., from sensor 27 to sensor 29, or from sensor 29 to sensor 27, or in both directions, e.g., between sensors 27 and 29. Similar patterns of piezoelectric sensor activation are employed by the embodiment of FIG. 5.

In accordance with this disclosure, following a substantial change in temperature of the fluid flowing in the tube, the processor 21 responds immediately (some seconds depending on the flow rate and tube thickness) with the change of the temperature and to calculate the temperature corrected fluid flow rate of the flowing fluid. Moreover, a fluid flow sensing and bubble detecting apparatus as disclosed does not require the use of an ultrasonic transmission gel to operate on a tube or pipe; however, the apparatus may be used with ultrasonic transmission gel applied to the tube or pipe. Preferably, the tube T is a polyvinyl chloride (PVC) tube or a silicone tube; however, the fluid flow sensing and bubble detecting apparatus disclosed herein may be applied to other kinds of tubes or pipes, such as a thin polycarbonate connector. In accordance with this disclosure, the clam-shell housing 11 may be provided with a push-button operated latching mechanism 79 that latches the cover 7 to the main housing 3 to keep the cover 7 in a closed-position.

Figure 10:
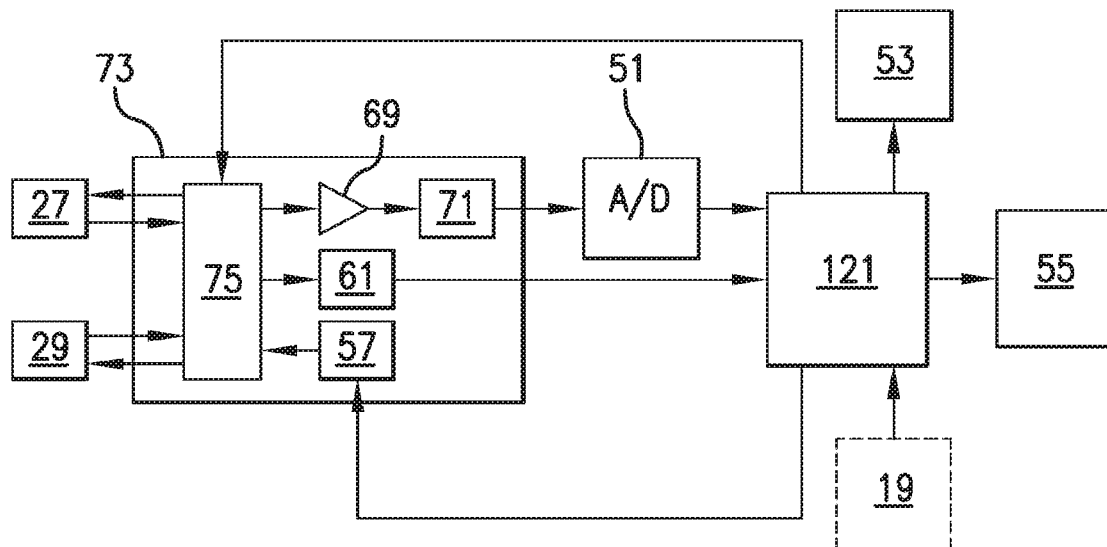
FIGS. 10 and 11 are schematic illustrations of the electronics of other non-limiting illustrative inventive embodiments of a fluid flow sensing and bubble detecting apparatus of disclosure.

FIG. 10 schematically illustrates another embodiment of a fluid flow sensing and bubble detecting apparatus in accordance with this disclosure. According to the embodiment of FIG. 10, paired piezoelectric sensors 27, 29 are operably connected to provide signal input and output to a multiplexing circuit 75 of the dual fluid flow rate and bubble detection circuit 73, which is connected to provide input into an amplifier 69 and a suitable circuit 71 for providing bubble detection data depending upon gating of the multiplexing circuit 75. Analog bubble detection data is input to the A/D converter 51 before being input to the processor 121 for the purposes of ascertaining the presence, or absence, of bubbles in the fluid F.

The paired piezoelectric sensors 27, 29 are also operably connected to provide signal input and output to the multiplexing circuit 75 in order to provide analog fluid flow rate data, when gated to do so, that is processed by the fluid flow rate data processing circuit 61, which comprises a timing circuit and other components that output a digital signal that is input to the processor 121 for the purpose of ascertaining the fluid flow rate Q of fluid F. The processor 121 is operably connected to output the calculated fluid flow rate Q and the results of bubble detection to an audio-visual display apparatus 53 and/or other device 55.

The processor 121 is operably connected to provide control signals to the generator 57 and to the multiplexing circuit 75, so the processor 121 controls operation of the multiplexer and the gating of the piezoelectric sensors 27, 29 as emitters and receivers, and the gating of output from the piezoelectric sensors 27, 29 for bubble detection or for fluid flow rate determination. Optionally, the processor 121 is also operably connected to receive digital temperature data directly from a digital temperature sensor, such as a Melexis MLX90614 temperature sensor, so that the processor 121 may calculate out a temperature corrected fluid flow rate $Q_{TC}$ of the flowing fluid F based on the digital temperature data generated by temperature sensor 19 and the digitally converted analog fluid flow rate data generated by piezoelectric sensors 27, 29. The processor 121 is operably connected to output the fluid flow rate Q (which is not corrected for temperature) or the temperature corrected fluid flow rate $Q_{TC}$ to the devices 53 and/or 55, depending upon whether the digital temperature sensor is employed.

Figure 11:
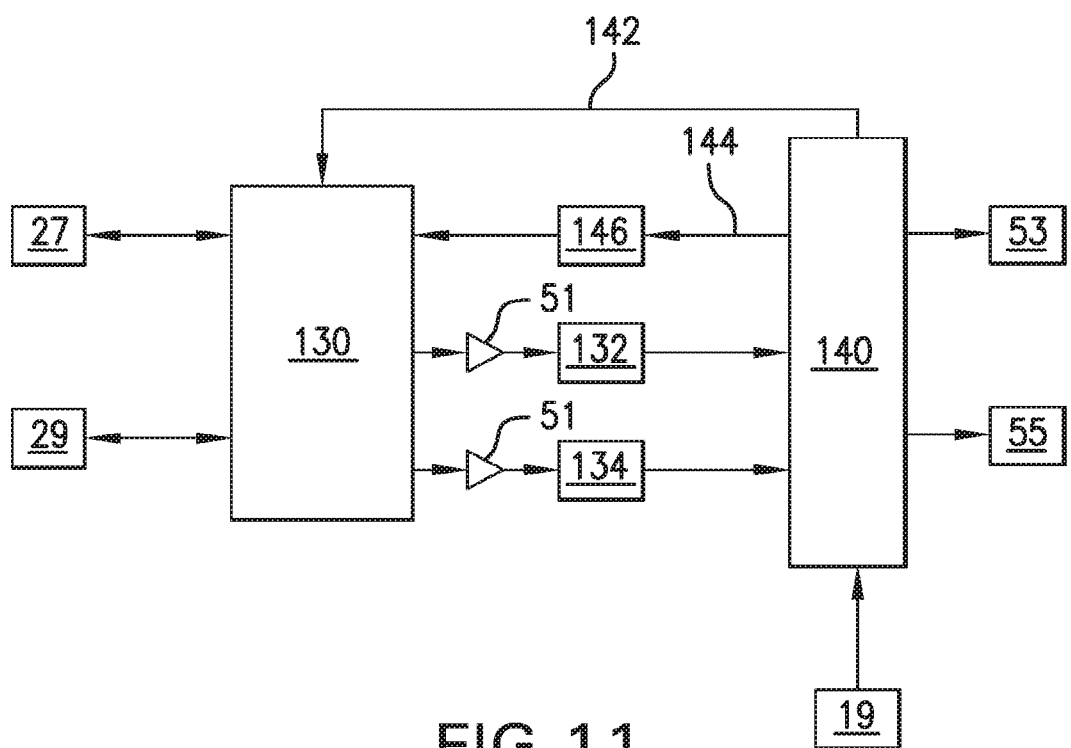

FIG. 11 schematically illustrates another embodiment of a fluid flow sensing and bubble detecting apparatus in accordance with this disclosure. According to the embodiment of FIG. 11, paired piezoelectric sensors 27, 29 are operably connected to provide signal input and output to a multiplexing circuit 130, which is connected to provide input to a bubble detection circuit 132 as bubble detection data, or input to a fluid flow rate determination circuit 134 as fluid flow rate data, depending upon gating of the multiplexing circuit 130. Amplifiers 51 are provided to amplify analog signals output from the multiplexer 130 to amplified signals before they are input into the bubble detection circuit 132 or the fluid flow rate determination circuit 134, each of which may include circuitry to convert the inputted analog signals into digital signals. The digital outputs from the bubble detection circuit 132 and the fluid flow rate determination circuit 134 are input to the processor 140 to be used, respectively, to determine the presence or absence of bubbles and to determine fluid flow rate. Because the processor 140 is operably connected to receive fluid temperature data from a digital temperature sensor 19, the fluid flow rate determined by the processor 140 may be a temperature corrected fluid flow rate $Q_{TC}$ of the flowing fluid F.

As shown in FIG. 11, the processor 140 is operably connected via line 142 to control operation of the multiplexer 130 and the processor 140 is operably connected via line 144 to control operation of the ultrasonic generator 146, which provides the ultrasonic signal that drives the piezoelectric sensors 27, 29. Results with respect to the presence or absence of bubble detection, and with respect to calculated temperature-corrected fluid flow rates, are output from the processor 140 to the audio-visual display apparatus 53 and/or other device 55.

Figure 12:
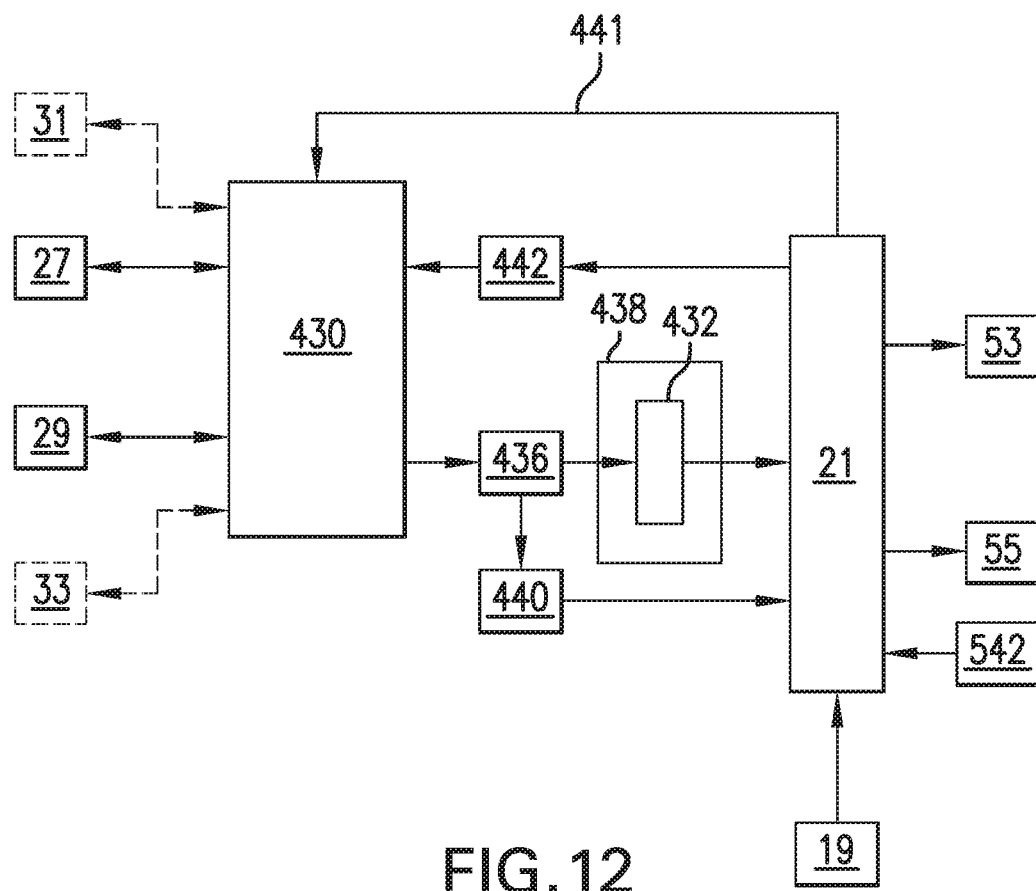
FIG. 12 is a schematic illustration of electronics of a blood flow sensing and bubble detecting apparatus in accordance with a non-limiting embodiment of this disclosure.

FIG. 12 illustrates a blood flow sensing and bubble detecting apparatus in accordance with another embodiment of this disclosure. The blood flow sensing and bubble detecting apparatus shown in FIG. 12 employs circuitry similar to that of the apparatus shown in FIG. 9. Thus, a description of like parts is not repeated for the sake of brevity. The blood flow sensing and bubble detecting apparatus of FIG. 12 is constructed for monitoring blood flow in a tube, or disposable in contact with blood, and is provided with a sensor 542 that measures the hematocrit or hemoglobin of blood. It does not matter whether sensor 542 is a hematocrit sensor or a hemoglobin sensor because there is a well-known relationship between hematocrit and hemoglobin so it is mathematically straightforward to convert hematocrit data to hemoglobin data, and to convert hematocrit data to hemoglobin data with a certain accuracy, using processor 21. For example, one commonly employed relationship for converting hemoglobin to hematocrit is to multiply the hemoglobin value by three to get the hematocrit value, although other relationships may be used that take into account additional factors. Flow compensation can thus be achieved by either measuring hemoglobin and/or hematocrit.

Blood viscosity, hemoglobin/hematocrit and/or density are known to affect blood flow measurements, and blood viscosity and/or density are affected by blood temperature and blood hematocrit or hemoglobin. Thus, blood flow measuring error related to blood temperature, and/or to blood hematocrit or hemoglobin, can be corrected by processor 21, which is programmed to correct blood flow measurements for the effects of blood temperature and/or blood hematocrit or hemoglobin. Hematocrit or hemoglobin data measured by sensor 542, depending upon whether sensor 542 is a hemoglobin sensor or a hematocrit sensor, is input to the processor 21, which is programmed to correct blood flow measurements appropriately for hematocrit or hemoglobin level of the flowing blood. Blood temperature data measured by temperature sensor 19 is input to processor 21, which is programmed to correct blood flow measurements for temperature of the flowing blood. Because processor 21 receives data input from both sensors 19 and 542, the processor 21 can be programmed to correct blood flow measurements for both blood temperature and either hematocrit or hemoglobin. Of course, processor 21 may be programmed to correct blood flow measurements based on just the blood temperature data input from sensor 19, or to correct blood flow measurements based on just hematocrit and/or hemoglobin data input from sensor 542, or it may be programmed to correct blood flow measurements based on both the blood temperature data input from sensor 19 and the hematocrit and/or hemoglobin data input from sensor 542.

Figure 13:
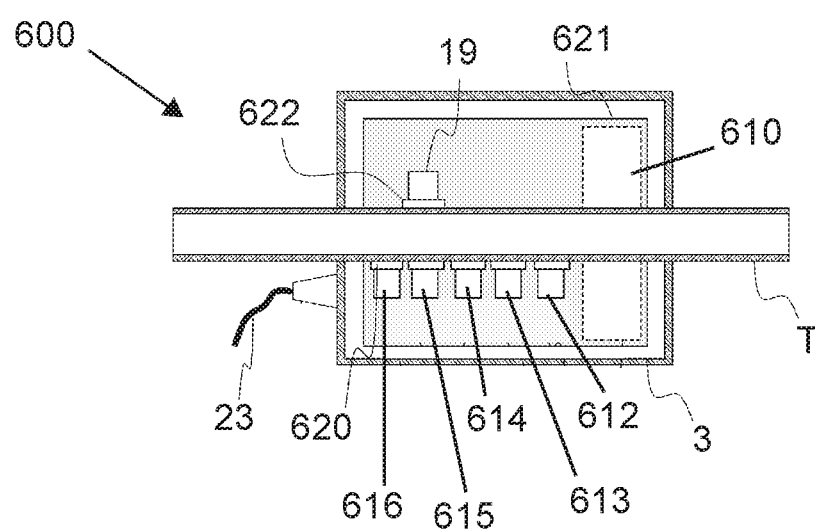
FIG. 13 is a schematic illustration of a sensor array 600 for measuring blood temperature and hematocrit/hemoglobin that may be used with an ultrasonic piezoelectric sensor array 610.

The hematocrit/hemoglobin sensor 542 may be constructed as a spectro-photomeric sensor that determines hematocrit or hemoglobin based on the intensity of the absorption and reflection of light at different wavelengths because light at different wavelengths are absorbed and reflected in different intensities depending upon the hematocrit value and hemoglobin value of the blood. For example, sensor 542 may be constructed from a plurality of light emitting diodes (LEDs) 612, 614, 616 and corresponding photodetectors 613, 615, as shown in FIG. 13, or sensor 542 may be a spectrometer used for hematocrit and/or hemoglobin measurement. Thus, different wavelengths may be used to measure hematocrit and/or hemoglobin. For example, LED 612 may have a wavelength of 1385 nm, and LED 614 may have a wavelength of 806 nm. The photodetector 613 may be an InGaAs photodetector. The LEDs and photodetectors are provided with protective windows 620, each with an appropriate wavelength filtering coating. Each of the sensor 19 and photodetectors 613, 615, and ultrasonic measurement cell 610, are operably connected to input measured data to processor 21, which may be a component of a printed circuit board 621. The ultrasonic measurement cell 610 corresponds to one of the ultrasonic piezoelectric sensor arrays shown by FIG. 6A, 6B, 6C or 6D.

In accordance with an embodiment of this disclosure, an oxygen saturation sensor may be connected to processor 21 so that oxygen saturation measurements may be used to increase the accuracy of the hematocrit measurement. To measure hematocrit, hemoglobin, oxygen saturation and blood temperature, a MAQUET BMU 40 venous probe or the Venous Probe of MAQUET CARDIOHELP may be connected to provide hematocrit, hemoglobin, oxygen saturation and blood temperature data input to the processor 21. In accordance with another embodiment of this disclosure, the LED 616 may have a wavelength of 659 nm and the photodetector 615 may be a silicon photodetector.

Sensor 19 may be a non-invasive IR-sensor temperature sensor, or it may be a negative temperature coefficient (NTC) thermistor with YSI400 calibration curve (such as when there is a metal well in the disposable), or other suitable temperature sensor. Sensor 19 may be either in direct contact with tubing T, or it may be protected against blood with an IR-window made of a material selected from the group consisting of silicon or zinc selenide (ZnSe) or zinc sulfide (ZnS) or other suitable material that is, to a certain extent, transparent for infrared light.

Figure 14:
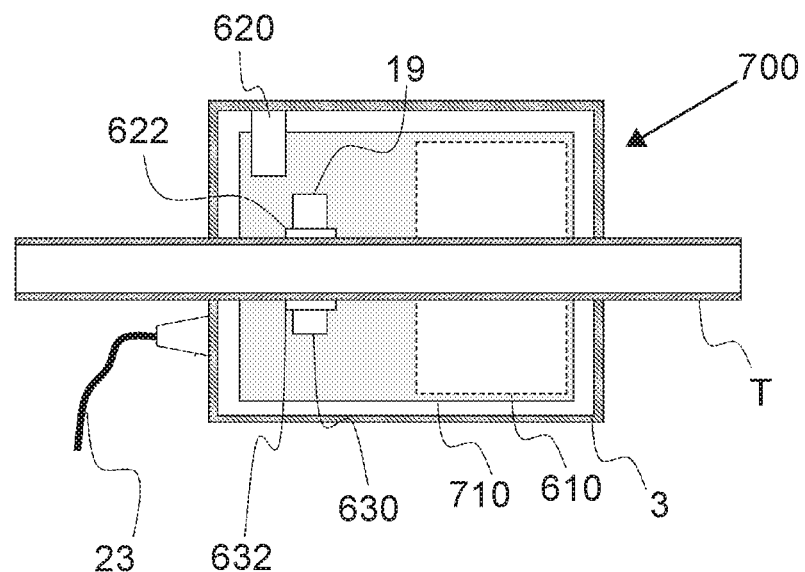
FIG. 14 is a schematic illustration of a sensor array 700 for measuring fluid temperature that may be used with an ultrasonic piezoelectric sensor array 610.

FIG. 14 is a schematic illustration of a temperature sensor array 700 that may be used with an ultrasonic piezoelectric sensor array 610 to measure temperature-corrected fluid flow rates. This temperature sensor array 700 does not employ a hematocrit/hemoglobin sensor, so it is usable with blood and with fluids other than blood. According to the embodiment of temperature sensor array 700, an ultrasonic measurement cell 610 and temperature sensor 19 are operably connected to input measured data to processor 21, which is a component of a printed circuit board 710, so that blood flow can be calculated and corrected for blood temperature, and air bubbles can be detected. The non-invasive IR-temperature sensor 19 can have direct contact with the fluid, or it can be protected against dust and moisture with an infrared transparent window 622. The infrared transparent window 622 may be made from various infrared transparent materials, such as zinc sulfide (ZnS), zinc selenium, or silicon.

The non-invasive IR-temperature sensor 19 may be influenced by ambient temperature in a way that decreases measurement accuracy. In accordance with an embodiment of this disclosure, the temperature sensor array 700 may optionally be provided with an ambient temperature sensor 620, such as an NTC thermistor or a platinum resistance thermistor (PT100 thermistor) or other suitable thermistor, which is operably connected to send measured ambient temperature data to the processor 21. The ambient temperature sensor 620 is disposed to measure ambient temperature, and employs a resistive thermistor, such as an NTC thermistor or PT100 thermistor. The processor 21 uses the ambient temperature data measured by the ambient temperature sensor 620 to adjust blood flow temperature data provided by the IR-temperature sensor 19 for ambient temperature, or to adjust temperature-corrected blood flow calculations for ambient temperature.

The non-invasive IR-temperature sensor 19 measures mostly infrared light of the tubing T because infrared light emitted by the fluid is mostly absorbed by the tubing's wall. Measurement of infrared light of the tubing is affected by the temperature of the tubing T. In order to improve accuracy of the temperature measurement of the fluid, an additional temperature sensor 630 may be disposed to measure the temperature of the wall of the tube T. This temperature sensor 630 may be a resistive thermistor, such as an NTC thermistor or a PT100 thermistor, and is disposed on a thermal conductive part 632 of the housing 3, which has good thermal conductivity such as may be provided by a metal. Tube wall temperature data measured by temperature sensor 630 is input to the processor 21, which uses the tube wall temperature data to correct measured values of the fluid temperature for the effect of tube wall temperature, or which uses the tube wall temperature data to adjust the temperature-corrected blood flow calculations for temperature of the tubing wall.

Figure 15:
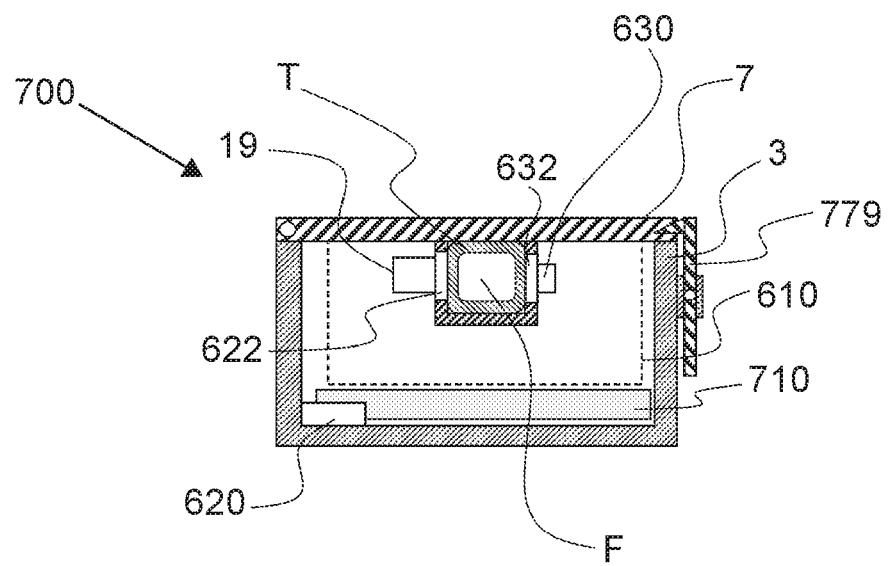
FIG. 15 is a cross-sectional illustration of sensor array 700 for measuring fluid temperature that may be used with an ultrasonic piezoelectric sensor array 610.
Figure 16:
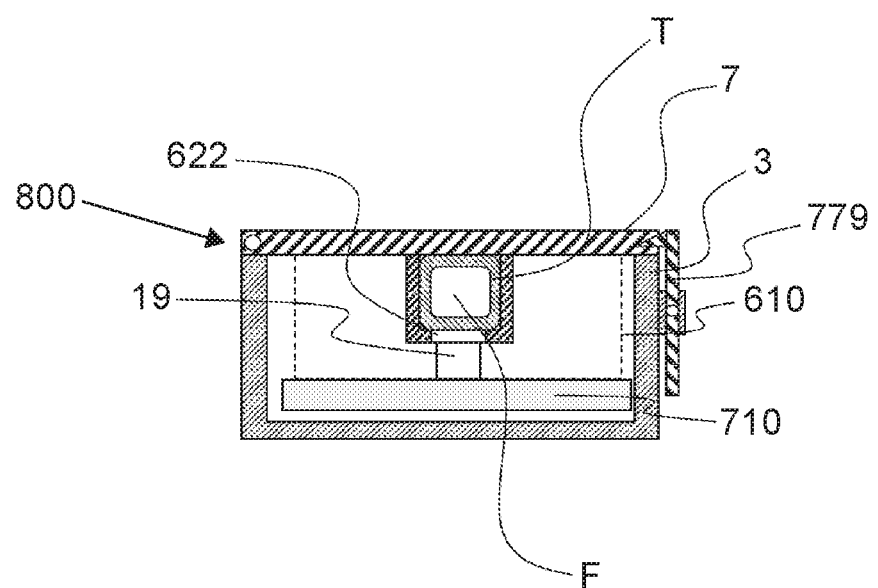
FIG. 16 is a cross-sectional illustration of a sensor array 800 for measuring fluid temperature that may be used with an ultrasonic piezoelectric sensor array 610.

FIG. 15 is a schematic cross-sectional illustration of temperature sensor array 700 that is used with an ultrasonic piezoelectric sensor array 610. This cross-sectional view shows one advantageous non-limiting relationship between the temperature sensors 19 and 632 and the compressed tube T filled with fluid F, such as blood, or water, and possibly some gas. The cover 7 of the housing 3 may be provided with a locking mechanism 779. FIG. 16 is a schematic cross-sectional illustration of temperature sensor array 800 that is used with an ultrasonic piezoelectric sensor array 610. This cross-sectional view shows one advantageous non-limiting relationship between one or more temperature sensors 19 and the compressed tube T filled with fluid F, such as blood, or water, and possibly some gas.

In accordance with this disclosure, a non-limiting embodiment pertaining to a method of monitoring a fluid flowing through a tube that is a component of medical equipment, or that is connected to medical equipment, is provided wherein the method includes the steps of: (a) operating a fluid flow sensing and bubble detecting apparatus that comprises a sensor apparatus disposed within a housing in order to generate fluid flow rate data and fluid temperature data with respect to fluid flowing within a tube or pipe, wherein the sensor apparatus includes a first sensor operable to measure a flow rate of a fluid, a second sensor operable to detect bubbles in the flowing fluid, and a temperature sensor operable to measure a temperature of the flowing fluid; and (b) calculating a temperature corrected fluid flow rate from the generated fluid flow rate data and the fluid temperature data, wherein calculation of the temperature corrected fluid flow rate is performed by a processor of the fluid flow sensing and bubble detecting apparatus. According to this method, the calculated temperature has an accuracy of about ±0.5° C., and the processor calculates a temperature corrected fluid flow rate immediately (some seconds to about 20 seconds) following a substantial change in temperature of the fluid flowing in the tube, although the temperature corrected fluid flow rate calculated immediately after the temperature change may not represent a steady state, and it may take more time to reflect a steady state following the temperature change. Furthermore, this method may further include the step of: (c) detecting the presence of one or more gas bubbles in the fluid flowing within the tube or pipe, wherein the second sensor detects the one or more gas bubbles. In addition, the first sensor measures the flow rate of the fluid flowing within the pipe or tube, and the temperature sensor measures the temperature of the fluid flowing within the pipe or tube.

However, it is possible for the first sensor to measure both the flow rate of the fluid flowing within the pipe or tube, and also detect the presence (or absence) of bubbles in fluid flowing within the pipe or tube, when the first sensor constitutes a pair of offset ultrasonic piezoelectric detectors, or even two or more pairs of ultrasonic piezoelectric sensors. In this context, a pair of offset ultrasonic piezoelectric detectors constitutes two ultrasonic piezoelectric detectors arranged on the exterior of the tube T so there is a non-orthogonal angle between the direction of fluid flow and the path(s) of the transmitted ultrasonic signals. Thus, in accordance with another non-limiting method embodiment, a method of monitoring a fluid flowing through a tube that is a component of medical equipment, or that is connected to medical equipment, is provided wherein the method includes the steps of: (a) operating a fluid flow sensing and bubble detecting apparatus that comprises a sensor apparatus disposed within a housing in order to generate fluid flow rate data and fluid temperature data with respect to fluid flowing within a tube or pipe, wherein the sensor apparatus includes a first sensor operable in a first mode to measure a flow rate of a fluid and operable in a second mode to detect bubbles in the flowing fluid, and a temperature sensor operable to measure a temperature of the flowing fluid; and (b) calculating a temperature corrected fluid flow rate from the generated fluid flow rate data and the fluid temperature data, wherein calculation of the temperature corrected fluid flow rate is performed by a processor of the fluid flow sensing and bubble detecting apparatus. According to this method, the calculated temperature has an accuracy of about ±0.5° C., and the processor calculates the temperature corrected fluid flow rate immediately (some seconds to about 20 seconds) following a substantial change in temperature of the fluid flowing in the tube. As discussed above, the calculated temperature corrected fluid flow rate obtained immediately after the temperature change may not correspond to a steady state, so it may take a longer period of time for the calculated temperature corrected fluid flow rate to reflect a steady state after the temperature change. Furthermore, this method may further include the step of: (c) detecting the presence of one or more gas bubbles in the fluid flowing within the tube or pipe, wherein the first sensor detects the one or more gas bubbles. In addition, the first sensor measures the flow rate of the fluid flowing within the pipe or tube, and the temperature sensor measures the temperature of the fluid flowing within the pipe or tube.

Another non-limiting method embodiment of this disclosure pertains to a method of monitoring blood flowing through a tube or disposable that is a component of medical equipment or that is connected to medical equipment, wherein the method comprises the steps of: (a) operating a blood flow sensing and bubble detecting apparatus that comprises a sensor apparatus disposed within a housing in order to generate blood flow rate data and blood temperature data and blood hematocrit or hemoglobin data, and optionally also oxygen saturation data, with respect to blood flowing within a tube or pipe, wherein the sensor apparatus includes a first sensor operable to measure a flow rate of blood and to detect bubbles in the flowing blood, and a temperature sensor operable to measure a temperature of the flowing blood, and a blood sensor operable to measure hematocrit or hemoglobin in the flowing blood; and (b) calculating a corrected blood flow rate from the generated blood flow rate data and the blood temperature data and the blood hematocrit or hemoglobin data, wherein calculation of the corrected blood flow rate is performed by a processor of the fluid flow sensing and bubble detecting apparatus, wherein the corrected blood flow rate is corrected for blood temperature, or blood hematocrit or hemoglobin, or both blood temperature and blood hematocrit or hemoglobin. Furthermore, this method may further include the step of: (c) detecting the presence of one or more gas bubbles in the blood flowing within the tube or pipe, wherein the first sensor detects the one or more gas bubbles. In accordance with another embodiment of this disclosure, these method embodiments may involve calculation of the corrected blood flow rate in a manner that employs oxygen saturation data measured by the blood sensor so that the corrected blood flow rate is compensated for the affect of oxygen saturation on the blood hematocrit or hemoglobin data.

Figure 8:
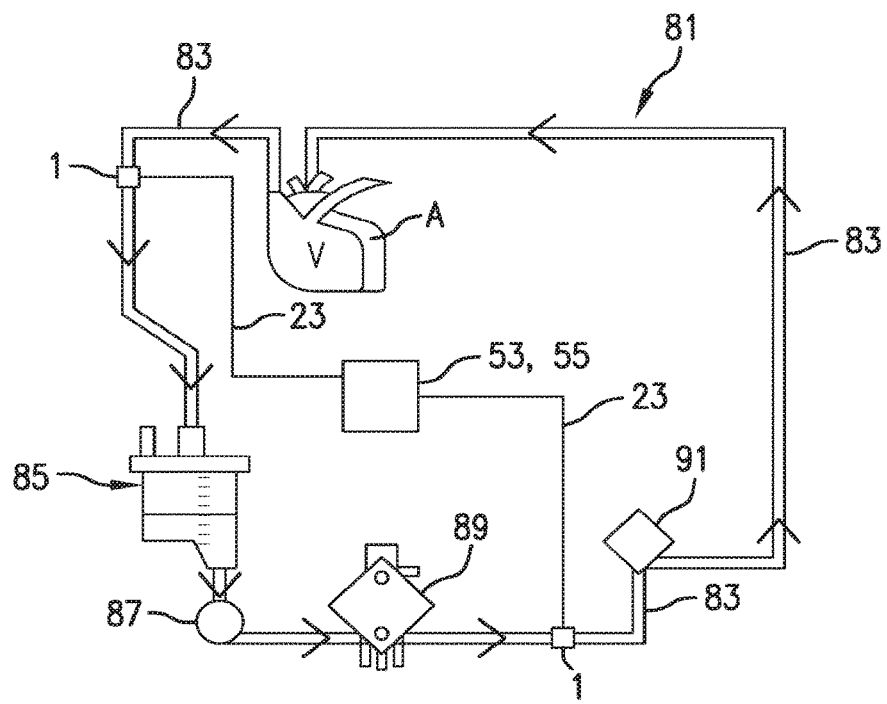
FIG. 8 is a schematic illustration of an extracorporeal blood flow circuit of a coronary bypass system that employs a fluid flow sensing and bubble detecting apparatus of this disclosure.

One non-limiting application of a fluid flow sensing and bubble detecting apparatus, such as described above, is in an extracorporeal blood flow circuit 81 of a coronary bypass system, such as is used during coronary bypass surgery. The blood flow circuit 81 of the coronary bypass system of FIG. 8 includes surgical tubing 83 constructed of materials suitable for transporting blood, and optionally coated with materials to prevent blood from clotting, which connects the venous system V of a patient to the arterial system A of the patient. It should be noted that while a patient is referenced in various embodiments, a non-human patient or patient simulator such as a practice mannequin may be interchangeably used in place of a human patient. The blood flow circuit 81 further includes a venous hardshell reservoir 85 for venous blood, and a centrifugal pump 87 that draws venous blood from the reservoir 85 and pumps it through an oxygenator 89, which increases the oxygen content of the blood. The blood flow circuit 81 also includes an arterial filter 91, which filters blood oxygenated by oxygenator 89 before it returns to the arterial system of the patient. The blood flow circuit 81 further includes two fluid flow sensing and bubble detecting apparatuses 1 clamped to the exterior of tubing 83 to measure blood flow rate, detect bubbles in the blood, and measure the temperature of blood leaving the patient on the venous side and entering the patient on the arterial side. Each of the fluid flow sensing and bubble detecting sensor arrays 13 are connected by transmission lines 23 to an audio-visual display apparatus 53 and/or other display device 55 so that fluid temperature, temperature corrected fluid flow rates $Q_{TC}$ and bubble detection results can be displayed. In this way, the blood flowing in the blood flow circuit 81 may be monitored for its rate of flow, temperature and the presence of air bubbles, which facilitates operation of the blood flow circuit 81 of the coronary bypass system by a clinical perfusionist during coronary bypass surgery, thereby improving patient care.

While the present disclosure describes various inventive embodiments and/or examples, it is not intended that these embodiments limit the scope of the invention, as it is defined by the appended claims. For example, while an embodiment of a fluid flow sensing and bubble detecting apparatus has been described with application to a coronary bypass system, such an embodiment is not limited to application to a coronary bypass system. Such a fluid flow sensing and bubble detecting apparatus may be applied to other systems through which a patient's blood flows through tubing, such as a dialysis system, and ECMO system, and the like. Furthermore, such a fluid flow sensing and bubble detecting apparatus may be applied to systems that do not involve the flow of blood, such as through cell culturing systems in which cell culture medium flows through tubing at a desired rate, temperature and bubble free, or in food processing systems in which fluid flows through a tube at a desired flow rate and temperature, and monitored for the presence of bubbles, or in a chemical processing system in which various reaction substrates flow in a liquid medium though a tube at a desired flow rate and temperature and monitored for the presence or absence of bubbles.

Moreover, the embodiment of a fluid flow sensing and bubble detecting apparatus illustrated in FIG. 5 may be modified to include the piezoelectric sensors 27, 29, 31 and 33, the two dual fluid flow rate and bubble detection circuits 73, and no temperature measuring circuit 47 and no temperature sensor 19 or infrared sensor element 37 in accordance with another non-limiting embodiment. Similarly, the embodiment of a fluid flow sensing and bubble detecting apparatus illustrated in FIG. 7 may be modified to include piezoelectric sensors 27, 29, one dual fluid flow rate and bubble detection circuit 73, and no temperature measuring circuit 47 and no temperature sensor 19 or infrared sensor element 37.

In accordance with another non-limiting embodiment, the multiplexer 43, the A/D converter 51, and circuits 45, 47, and 49 are included as components of the signal processing circuit 26, and are housed with the processor 21 and not within the clam-shell housing 11 with the sensors 27, 29, 31, 33 and 37. On the other hand, in accordance with another non-limiting embodiment, the multiplexer 43, the A/D converter 51, and the circuits 45, 47, and 49 are housed with the sensors 27, 29, 31, 33 and 37 in the clam-shell housing 11.

The embodiments of FIGS. 4 and 5 employ two pairs of piezoelectric sensors 27, 29 and 31, 33. However, additional embodiments of fluid flow sensing and bubble detecting apparatuses, in accordance with this disclosure, may include more than two pairs of piezoelectric sensors. For example, it is within the scope of this disclosure to modify the embodiments corresponding to FIGS. 4 and 5, respectively, so that each employs three pairs of piezoelectric sensors, or four pairs of piezoelectric sensors, or five pairs of piezoelectric sensors, or six pairs of piezoelectric sensors, etc. The additional pairs of piezoelectric sensors may be used, in accordance with a modified embodiment of FIG. 4, as all additional bubble detecting sensors, or as all additional flow rate measuring sensors, or some of the additional paired piezoelectric sensors may be used for bubble detection and some of the additional paired piezoelectric sensors may be used for flow rate determination. So, for example, the embodiment of FIG. 4 may be modified to employ four pairs of piezoelectric sensors, wherein one pair 27, 29 is used for fluid flow rate measuring and one pair 31, 33 is used for bubble detection, and either the remaining two pairs are both used for flow rate measuring, or are both used for bubble detection, or one is used for flow rate measuring and one is used for bubble detection. In accordance with a modified embodiment of FIG. 5, all of the additional paired piezoelectric sensors may be used as dual use flow rate measuring and bubble detecting sensors, whether the modified embodiment employs three pairs of piezoelectric sensors, or four pairs of piezoelectric sensors, or five pairs of piezoelectric sensors, or six pairs of piezoelectric sensors, etc.

While this disclosure provides multiple exemplary embodiments, it will be understood by those skilled in the art that various changes may be made and equivalents may be substituted for elements thereof without departing from the scope of this disclosure. In addition, many modifications may be made to adapt a particular situation or material to the teachings of this disclosure without departing from the essential scope thereof. Therefore, it is intended that the invention, as defined in the appended claims, not be limited to any particular embodiment disclosed herein, but that the invention will include all embodiments falling within the scope of the claims. Also, in the drawings and the description, there have been disclosed exemplary embodiments and, although specific terms may have been employed, they are unless otherwise stated used in a generic and descriptive sense only and not for purposes of limitation. Moreover, the use of the terms first, second, etc. do not denote airy order or importance, but rather the terms first, second, etc. are used to distinguish one element from another. Furthermore, the use of the terms a, an, etc. do not denote a limitation of quantity, but rather denote the presence of at least one of the referenced item unless otherwise explicitly indicated.

We claim:

1. A fluid flow sensing and bubble detecting apparatus, comprising:

a housing provided with a channel configured to receive a tube through which fluid flows;

a sensor apparatus supported by the housing, wherein the sensor apparatus includes a first sensor operable to measure a flow rate of fluid and operable to detect bubbles in flowing fluid; and a temperature sensor operable to detect a temperature of the flowing fluid, wherein the temperature sensor comprises a non-invasive/non-contact infrared temperature sensor that measures temperature of fluid, whether flowing or standing, with an accuracy of about ±0.5° C.;

a processor operably connected to receive fluid flow rate data obtained by the first sensor, and operably connected to receive bubble detection data obtained by the first sensor, and operably connected to receive fluid temperature data obtained by the temperature sensor, wherein the first sensor comprises a pair of ultrasonic pulse emitter-receivers disposed to emit and receive ultrasonic pulses from each other, wherein in a first mode of operation the first sensor generates the bubble detection data from the ultrasonic pulses emitted from the pair of ultrasonic pulse emitter-receivers and in a second mode of operation the first sensor generates the flow rate data from the ultrasonic pulses emitted from the pair of ultrasonic pulse emitter-receivers, wherein the bubble detection data and the flow rate data are sent to the processor; and a first multiplexer connected to gate a fluid flow rate and bubble detection circuit and to gate a temperature measuring circuit, wherein the first sensor is associated with the fluid flow rate and bubble detection circuit and the infrared temperature sensor is associated with the temperature measuring circuit, wherein the fluid flow rate and bubble detection circuit comprises a second multiplexer operably connected to the pair of ultrasonic pulse emitter-receivers so as to gate operation of the pair of ultrasonic pulse emitter-receivers between the first mode of operation and the second mode of operation, wherein when a tube through which fluid is flowing is disposed in the channel of the housing, the first sensor measures the flow rate of the flowing fluid and detects bubbles in the flowing fluid, and the temperature sensor measures the temperature of the flowing fluid and the processor employs the fluid flow rate data and the fluid temperature data to calculate a temperature corrected fluid flow rate of the flowing fluid in the tube.

2. The apparatus of claim 1, further comprising:

a second sensor operable to measure the flow rate of fluid and operable to detect bubbles in the flowing fluid, wherein the second sensor is operably connected to the processor so the processor receives fluid flow rate data and bubble detection data obtained by the second sensor so that when the tube through which fluid flows is disposed in the channel of the housing, the processor receives fluid flow rate data obtained by the first sensor and fluid flow rate data obtained by the second sensor, and the processor receives bubble detection data from the first sensor and bubble detection data from the second sensor.

3. The apparatus of claim 2, wherein the processor calculates a temperature corrected fluid flow rate of the flowing fluid in the tube based on the fluid flow rate data obtained by the first sensor, and the fluid flow rate data obtained by the second sensor, and the fluid temperature data obtained by the temperature sensor, and the processor outputs the calculated temperature corrected fluid flow rate to a display apparatus.

4. The apparatus of claim 2, wherein the processor employs bubble detection data received from the first sensor and bubble detection data received from the second sensor to determine whether a bubble is present in the fluid flowing in the tube.

5. The apparatus of claim 1, wherein following a substantial change in temperature of the fluid flowing in the tube, within about a minute the processor of the apparatus is able to calculate the temperature corrected fluid flow rate of the flowing fluid at a new steady state.

6. A fluid flow sensing and bubble detecting apparatus, comprising:

a housing provided with a channel configured to receive a tube through which fluid flows;

a sensor apparatus supported by the housing, wherein the sensor apparatus includes a first sensor operable to measure a flow rate of fluid and operable to detect bubbles in flowing fluid and a temperature sensor operable to detect a temperature of the flowing fluid;

a processor operably connected to receive fluid flow rate data obtained by the first sensor, and operably connected to receive bubble detection data obtained by the first sensor, and operably connected to receive fluid temperature data obtained by the temperature sensor, wherein the first sensor comprises a pair of ultrasonic pulse emitter-receivers disposed to emit and receive ultrasonic pulses from each other, wherein in a first mode of operation the first sensor generates the bubble detection data from the ultrasonic pulses emitted from the pair of ultrasonic pulse emitter-receivers and in a second mode of operation the first sensor generates the flow rate data from the ultrasonic pulses emitted from the pair of ultrasonic pulse emitter-receivers; and a first multiplexer connected to gate a fluid flow rate and bubble detection circuit and to gate a temperature measuring circuit, wherein the fluid flow rate and bubble detection circuit is connected to receive data input signals from the pair of ultrasonic pulse emitter-receivers and the temperature measuring circuit is connected to receive data input signals from the temperature sensor, wherein the fluid flow rate and bubble detection circuit comprises a second multiplexer operably connected to the pair of ultrasonic pulse emitter-receivers so as to gate operation of the pair of ultrasonic pulse emitter-receivers between the first mode of operation and the second mode of operation, wherein when a tube through which fluid is flowing is disposed in the channel of the housing, the first sensor measures the flow rate of the flowing fluid and detects bubbles in the flowing fluid, the temperature sensor measures the temperature of the flowing fluid, and the processor employs the fluid flow rate data and the fluid temperature data to calculate a temperature corrected fluid flow rate of the flowing fluid in the tube.

7. The apparatus of claim 6, wherein the temperature sensor comprises an infra-red thermometer detector.

8. A method of monitoring a fluid flowing through a tube that is a component of medical equipment or that is connected to medical equipment, wherein the method comprises the steps of:

operating a fluid flow sensing and bubble detecting apparatus that comprises a sensor apparatus disposed within a housing in order to generate fluid flow rate data and fluid temperature data with respect to fluid flowing within a tube or pipe, wherein the sensor apparatus includes a first sensor operable to measure a flow rate of a fluid and to detect bubbles in the flowing fluid, and a temperature sensor operable to measure a temperature of the flowing fluid, wherein the first sensor comprises a pair of ultrasonic pulse emitter-receivers disposed to emit and receive ultrasonic pulses from each other, wherein in a first mode of operation the first sensor generates the bubble detection data from the ultrasonic pulses emitted from the pair of ultrasonic pulse emitter-receivers and in a second mode of operation the first sensor generates the flow rate data from the ultrasonic pulses emitted from the pair of ultrasonic pulse emitter-receivers, wherein the bubble detection data and the flow rate data are sent to the processor, and wherein a first multiplexer gates operation of the first sensor and the temperature sensor and a second multiplexer gates operation of the pair of ultrasonic pulse emitter-receivers between the first mode of operation and the second mode of operation; and calculating a temperature corrected fluid flow rate from the generated fluid flow rate data and the fluid temperature data, wherein calculation of the temperature corrected fluid flow rate is performed by a processor of the fluid flow sensing and bubble detecting apparatus.

9. The method of claim 8, further comprising the step of:

detecting the presence of one or more gas bubbles in the fluid flowing within the tube or pipe, wherein the first sensor detects the one or more gas bubbles.

10. The apparatus of claim 6, wherein the temperature sensor comprises a light emitting diode and a light receiving element disposed to receive light from the light emitting diode.

* * * * *